(12) United States Patent
Johnson et al.

(10) Patent No.: US 8,972,047 B2
(45) Date of Patent: Mar. 3, 2015

(54) PHARMACEUTICAL DISPENSING SYSTEMS AND GRAPHICAL USER INTERFACES ASSOCIATED WITH SAME

(75) Inventors: Matthew Johnson, Raleigh, NC (US); Harold Lindsey, Chapel Hill, NC (US); Megan Dunigan, Raleigh, NC (US); Justin Lallinger, Durham, NC (US); John Kirk Hammond, Jr., Raleigh, NC (US)

(73) Assignee: Parata Systems, LLC, Durham, NC (US)

( * ) Notice: Subject to any disclaimer, the term of this patent is extended or adjusted under 35 U.S.C. 154(b) by 1048 days.

(21) Appl. No.: 12/463,637

(22) Filed: May 11, 2009

(65) Prior Publication Data
US 2009/0287350 A1    Nov. 19, 2009

Related U.S. Application Data

(60) Provisional application No. 61/053,921, filed on May 16, 2008, provisional application No. 61/053,735, filed on May 16, 2008, provisional application No. 61/077,661, filed on Jul. 2, 2008, provisional application No. 61/105,529, filed on Oct. 15, 2008.

(51) Int. Cl.
| | |
|---|---|
| *G06F 17/00* | (2006.01) |
| *G07F 11/00* | (2006.01) |
| *G06F 19/00* | (2011.01) |
| *G07F 11/30* | (2006.01) |
| *G07F 11/44* | (2006.01) |
| *G07F 11/62* | (2006.01) |
| *G07F 17/00* | (2006.01) |

(52) U.S. Cl.
CPC .......... *G07F 11/002* (2013.01); *G06F 19/3462* (2013.01); *G07F 11/30* (2013.01); *G07F 11/44* (2013.01); *G07F 11/62* (2013.01); *G07F 17/0092* (2013.01)
USPC ............ 700/236; 700/242; 700/241; 700/244

(58) Field of Classification Search
CPC ..................................................... G06F 19/3462
USPC .................................. 700/236, 241, 244, 242
See application file for complete search history.

(56) References Cited

U.S. PATENT DOCUMENTS

| | | | |
|---|---|---|---|
| 2,002,753 A | 5/1935 | Parks et al. |
| 2,442,025 A | 5/1948 | Smith |
| 3,194,431 A | 7/1965 | Garvin |
| 3,938,700 A | 2/1976 | Camp et al. |
| 4,232,800 A | 11/1980 | Martin et al. |

(Continued)

*Primary Examiner* — Michael K Collins
(74) *Attorney, Agent, or Firm* — Myers Bigel Sibley & Sajovec

(57) ABSTRACT

A pharmaceutical dispensing system includes a frame having first and second opposed sides, a plurality of cells configured to house pharmaceutical pills, a first touch screen display on the frame first side, and a second touch screen display on the frame second side. A plurality of dispensing shelves configured to receive filled pill containers are accessible from the second side of the frame for removal of pill containers therein. The pharmaceutical dispensing system includes a processor and memory coupled thereto. A computer program resides in the memory and is executable by the processor for displaying a cell inventory graphical user interface (GUI) within the first touch screen display, and a series of GUIs within the second touch screen display that include status information about a prescription order at a respective stage of completion by the pharmaceutical dispensing system.

19 Claims, 33 Drawing Sheets

(56) References Cited

U.S. PATENT DOCUMENTS

| | | | | |
|---|---|---|---|---|
| 4,303,179 | A | 12/1981 | Spring | |
| 4,546,901 | A | 10/1985 | Buttarazzi | |
| 4,694,230 | A | 9/1987 | Slocum et al. | |
| 4,740,025 | A | 4/1988 | Nelson | |
| 4,782,274 | A | 11/1988 | Teegarden et al. | |
| 4,812,629 | A | 3/1989 | O'Neil et al. | |
| 5,208,762 | A * | 5/1993 | Charhut et al. | 700/216 |
| 5,337,919 | A | 8/1994 | Spaulding et al. | |
| 5,593,267 | A * | 1/1997 | McDonald et al. | 414/273 |
| 5,720,154 | A * | 2/1998 | Lasher et al. | 53/411 |
| 5,771,657 | A | 6/1998 | Lasher et al. | |
| 5,907,493 | A * | 5/1999 | Boyer et al. | 700/231 |
| 6,202,923 | B1 | 3/2001 | Boyer et al. | |
| 6,370,841 | B1 | 4/2002 | Chudy et al. | |
| RE37,829 | E | 9/2002 | Charhut et al. | |
| 6,522,945 | B2 * | 2/2003 | Sleep et al. | 700/225 |
| 6,742,671 | B2 | 6/2004 | Hebron et al. | |
| 7,228,198 | B2 | 6/2007 | Vollm et al. | |
| 7,530,211 | B2 * | 5/2009 | McErlean et al. | 53/505 |
| 7,720,569 | B2 * | 5/2010 | Forrester et al. | 700/241 |
| 7,783,383 | B2 * | 8/2010 | Eliuk et al. | 700/245 |
| 7,805,217 | B2 * | 9/2010 | Chudy et al. | 700/237 |
| 7,860,724 | B2 * | 12/2010 | Chudy et al. | 705/2 |
| 7,912,582 | B1 * | 3/2011 | Holtje et al. | 700/242 |
| 8,215,540 | B2 * | 7/2012 | Szesko et al. | 235/375 |
| 8,571,886 | B2 * | 10/2013 | Chudy et al. | 705/2 |
| 2004/0088187 | A1 * | 5/2004 | Chudy et al. | 705/2 |
| 2004/0133705 | A1 | 7/2004 | Broussard et al. | |
| 2005/0033606 | A1 * | 2/2005 | Miller | 705/2 |
| 2006/0161298 | A1 * | 7/2006 | DiMaggio | 700/244 |
| 2006/0265102 | A1 * | 11/2006 | Bain | 700/237 |
| 2007/0208595 | A1 * | 9/2007 | Ohmura et al. | 705/2 |
| 2008/0125897 | A1 * | 5/2008 | DiGianfilippo et al. | 700/110 |
| 2009/0043421 | A1 * | 2/2009 | Parrish et al. | 700/241 |
| 2011/0131056 | A1 * | 6/2011 | Chudy et al. | 705/2 |

\* cited by examiner

| REPLENISH CELL WIZARD | |
|---|---|
| [1] CELL | 1E |
| [2] DRUG | 000872772 |
| [3] LOT # | 1234567 |
| [4] LOT EXPIRATION | 07/2009 |
| [5] ENTER INVENTORY | |
| [6] FILL CELL AND CLOSE CELL DOOR | |

500

CURRENT INVENTORY:
66
MAXIMUM CAPACITY:
786
MAXIMUM ADDITION:
720

FIG. 13D

NEW CELL WIZARD

1. NEW CELL
2. DRUG      000935211
3. LOT #     qwerty
4. LOT EXPIRATION   02/2010
5. ENTER INVENTORY ADDITION
6. FILL CELL AND CLOSE CELL DOOR

700

LOT EXPIRATION DATE
- ○ JANUARY (1)      ○ 2008
- ⊘ FEBRUARY (2)    ○ 2009
- ○ MARCH (3)       ⊘ 2010
- ○ APRIL (4)        ○ 2011
- ○ MAY (5)          ○ 2012
- ○ JUNE (6)
- ○ JULY (7)
- ○ AUGUST (8)
- ○ SEPTEMBER (9)
- ○ OCTOBER (10)
- ○ NOVEMBER (11)
- ○ DECEMBER (12)

FIG. 15D

NEW CELL WIZARD

[1] NEW CELL
[2] DRUG          000935211
[3] LOT #         qwerty
[4] LOT EXPIRATION   02/2010
[5] INVENTORY ADDITION   [708]
[6] FILL CELL AND CLOSE CELL DOOR

700

CURRENT INVENTORY:
0
MAXIMUM CAPACITY:
708
MAXIMUM ADDITION:
708

[7] [8] [9]
[4] [5] [6]
[1] [2] [3]
[0] [ENTER]
[< BACKSPACE]

FIG. 15E

910a — BUILD REPORT
920a — VIEW REPORT
930a — SETUP

1. SELECT REPORT
- ○ AUDIT CELL
- ○ AUDIT DRUG
- ○ CELL SETTINGS
- ○ CLEARED SHELF
- ○ DISPENSE INFO
- ○ DRUG Rx HISTORY
- ○ DRUG SETUP
- ○ INVENTORY BY CELL

◁ 1/3 ▷

912

2. REPORT PARAMETERS
BEGIN DATE  9/29/2008
END DATE    9/29/2008

914
900
910

3. APPLY SORTING (OPTIONAL)

| COLUMNS | COLUMNS | COLUMNS |
|---|---|---|
| ○ ORDER NUMBER | ○ ORDER NUMBER | ○ ORDER NUMBER |
| ⊘ DRUG NAME | ○ DRUG NAME | ○ DRUG NAME |
| ○ DRUG CODE | ○ DRUG CODE | ○ DRUG CODE |
| ○ LOT NUMBER | ⊘ LOT NUMBER | ○ LOT NUMBER |
| ○ TOTAL QTY | ○ TOTAL QTY | ○ TOTAL QTY |
| ○ ENTRY DATE | ○ ENTRY DATE | ○ ENTRY DATE |
| ORDER | ORDER | ORDER |
| ⊘ ASC  ○ DESC | ⊘ ASC  ○ DESC | ⊘ ASC  ○ DESC |

[ABC] [SORT]                                [RESET]

BUILD REPORT

1. SELECT REPORT
- ○ AUDIT CELL
- ○ AUDIT DRUG
- ○ CELL SETTINGS
- ○ CLEARED SHELF
- ⊘ DISPENSE INFO
- ○ DRUG Rx HISTORY
- ○ DRUG SETUP
- ○ INVENTORY BY CELL

PHARMACEUTICAL DISPENSING SYSTEMS AND GRAPHICAL USER INTERFACES ASSOCIATED WITH SAME

RELATED APPLICATIONS

This application claims the benefit of and priority to U.S. Provisional Patent Application Nos. 61/053,921, filed May 16, 2008, 61/053,735, filed May 16, 2008, 61/077,661, filed Jul. 2, 2008, and 61/105,529, filed Oct. 15, 2008, the disclosures of which are incorporated herein by reference as if set forth in their entireties.

RESERVATION OF COPYRIGHT

A portion of the disclosure of this patent document contains material to which a claim of copyright protection is made. The copyright owner has no objection to the facsimile reproduction by anyone of the patent document or the patent disclosure, as it appears in the Patent and Trademark Office patent file or records, but reserves all other rights whatsoever.

FIELD OF THE INVENTION

The present invention relates generally to the dispensing of prescriptions of pharmaceuticals and, more particularly, to methods, systems and computer program products for automated dispensing of pharmaceuticals.

BACKGROUND

Pharmacy generally began with the compounding of medicines, which entailed the actual mixing and preparing of medications. Heretofore, pharmacy has been, to a great extent, a profession of dispensing, that is, the pouring, counting, and labeling of a prescription, and subsequently transferring the dispensed medication to the patient. Because of the repetitiveness of many of the pharmacist's tasks, automation of these tasks has been desirable. Various attempts have been made to automate the pharmacy environment. Different exemplary approaches are shown in U.S. Pat. No. 5,337,919 to Spaulding et al. and U.S. Pat. Nos. 6,006,946; 6,036,812 and 6,176,392 to Williams et al. As automated pharmacy machines have become substantially more robust and complex, operating software that is correspondingly robust is needed to facilitate user interaction and control of these machines.

SUMMARY

In view of the above discussion, automated and semi-automated pharmacy dispensing systems are provided. According to some embodiments of the present invention, a pharmaceutical dispensing system includes a frame having first and second opposed sides, a plurality of cells configured to house pharmaceutical pills, each of the cells being accessible from the first side of the frame for replenishment of pharmaceutical pills therein, a first touch screen display on the frame first side, and a second touch screen display on the frame second side. A plurality of dispensing shelves configured to receive filled pill containers are accessible from the second side of the frame for removal of pill containers therein.

The pharmaceutical dispensing system includes a processor and memory coupled thereto. A computer program resides in the memory and is executable by the processor for displaying a cell inventory graphical user interface (GUI) within the first touch screen display. The cell inventory GUI displays cell inventory information, and includes one or more GUI controls that are responsive to user touching for adding and/or modifying contents of the cells. Also, a computer program resides in the memory that is executable by the processor for displaying a series of graphical user interfaces (GUIs) within the second touch screen display. Each GUI in the series includes status information about a prescription order at a respective stage of completion of the prescription order by the pharmaceutical dispensing system.

The cell inventory GUI displays a graphical representation of each cell. In some embodiments, the graphical representation of each cell is displayed in a color that indicates an inventory level of pharmaceutical pills therein.

The series of GUIs include a pending queue GUI that displays information about pending prescription orders, a ready queue GUI that displays information about prescription orders that have been filled by the system, a complete queue GUI that displays information about filled prescription orders that have been removed from the dispensing shelves of the pharmaceutical dispensing system, and an incomplete queue GUI that displays information about unfilled prescription orders. The complete queue GUI includes a GUI control that, in response to user touching, displays a graphical representation of a dispensing shelf where a filled pill container is located. The series of GUIs includes a ready shelf GUI that is a graphical representation of the dispensing shelves of the pharmaceutical dispensing system. The ready shelf GUI also includes an array of icons, each icon associated with a respective dispensing shelf. Each icon displays a number of filled pill containers in a respective dispensing shelf.

In some embodiments, a computer program resides in the memory and is executable by the processor for displaying a report builder GUI within the first and second touch screen displays. The report builder GUI is configured to build reports relating to one or more of the following: pending prescription orders, filled prescription orders, cell inventory information, and drug information.

In some embodiments, a computer program resides in the memory and is executable by the processor for monitoring selected functions of the pharmaceutical dispensing system and for storing selected parameters associated with the monitored functions.

According to some embodiments of the present invention, a GUI for display within a touch screen display of a pharmaceutical dispensing system is configured to display status information about a prescription order at a respective stage of completion of the prescription order by the pharmaceutical dispensing system. The GUI includes a pending queue GUI, a ready queue GUI, a complete queue GUI, and an incomplete queue GUI. The pending queue GUI displays information about pending prescription orders. The ready queue GUI displays information about prescription orders that have been filled by the system. The complete queue GUI displays information about filled prescription orders that have been removed from dispensing shelves of the pharmaceutical dispensing system. The incomplete queue GUI displays information about unfilled prescription orders.

The GUI also includes a graphical representation of dispensing shelves of the pharmaceutical dispensing system, and an array of icons adjacent to the graphical representation of dispensing shelves. Each icon is associated with a respective dispensing shelf, and each icon displays a number of filled pill containers in a respective dispensing shelf.

According to some embodiments of the present invention, a GUI for display within a touch screen display of a pharmaceutical dispensing system is configured to display pharmaceutical pill inventory information. The pharmaceutical dispensing system includes a plurality of cells, and each cell is configured to contain a predetermined number of respective pharmaceutical pills. The GUI displays pharmaceutical pill inventory information for each cell, and at least one GUI control responsive to user touching for adding and/or modifying contents of each of the cells. In some embodiments, the pharmaceutical pill inventory information for each cell is displayed in a color that indicates an inventory level of pharmaceutical pills therein.

BRIEF DESCRIPTION OF THE DRAWINGS

FIGS. 17A-17G are GUIs that allow an operator of the pharmaceutical dispensing system of FIGS. 2-3 to build, view, print and export various reports, in accordance with some embodiments of the present invention.

DETAILED DESCRIPTION

Figure 1:
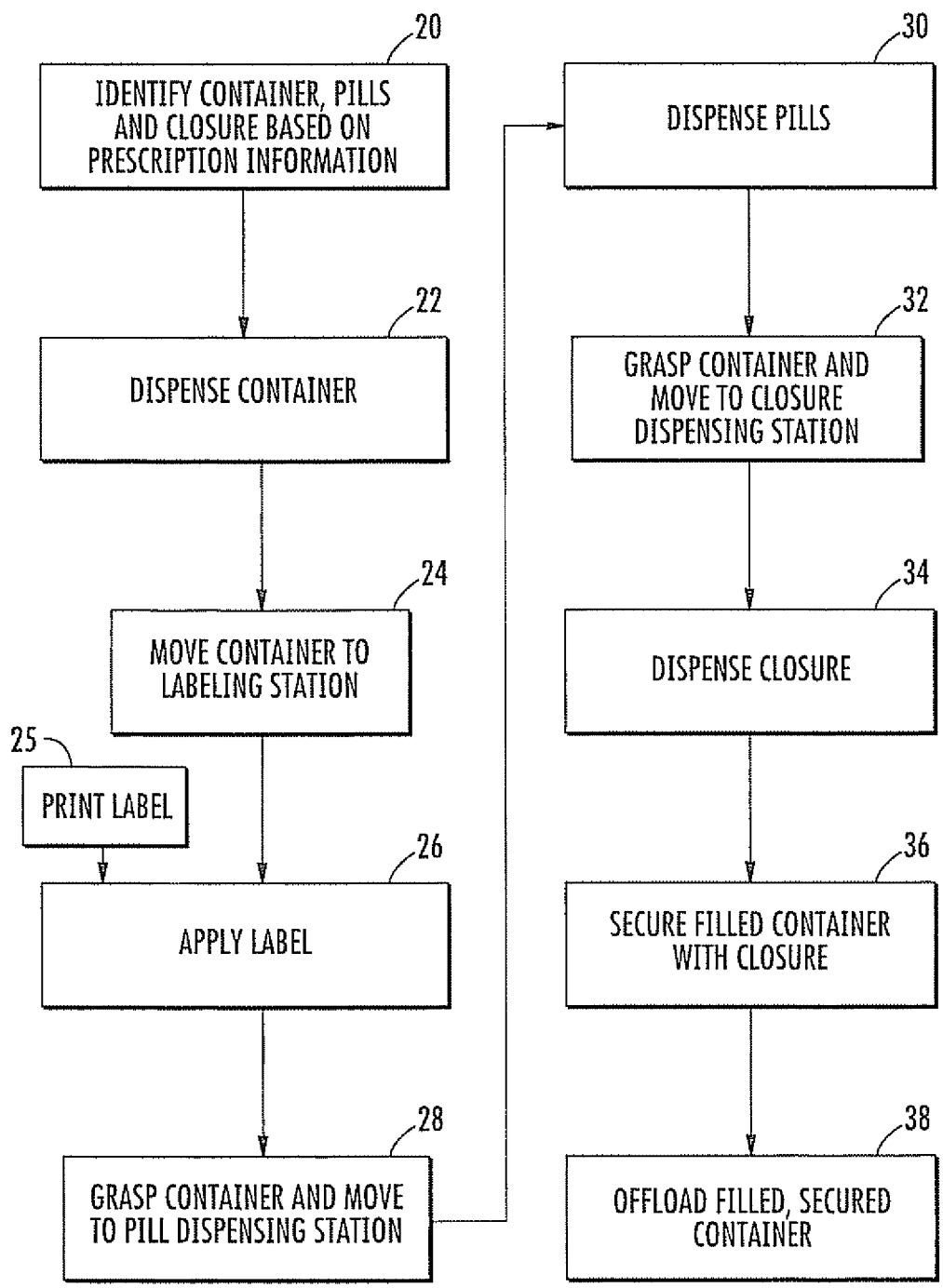
FIG. 1 is a flow chart depicting operations that can be carried out by a pharmaceutical dispensing system according to embodiments of the present invention.

The present invention now will be described more fully hereinafter with reference to the accompanying drawings, in which illustrated embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

As used herein, the singular forms "a," "an," and "the" are intended to include the plural forms as well, unless expressly stated otherwise. It will be further understood that the terms "includes," "comprises," "including," and/or "comprising," when used in this specification, specify the presence of stated features, steps, operations, elements, and/or components, but do not preclude the presence or addition of one or more other features, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

It will also be understood that, although the terms first, second, etc. may be used herein to describe various elements, these elements should not be limited by these terms. These terms are only used to distinguish one element from another. For example, a first GUI control could be termed a second GUI control, and, similarly, a second GUI control could be termed a first GUI control without departing from the teachings of the disclosure.

Unless otherwise defined, all terms (including technical and scientific terms) used herein have the same meaning as commonly understood by one of ordinary skill in the art to which this invention belongs. It will be further understood that terms such as those defined in commonly used dictionaries, should be interpreted as having a meaning that is consistent with their meaning in the context of the relevant art and will not be interpreted in an idealized or overly formal sense unless expressly so defined herein.

The term "container", as used herein, refers to any type of container including pill containers or vials used to fill a prescription, as well as "stock" bottles that contain pills used to refill cells on the replenishing side of a pharmacy dispensing system.

The term "pills" refers to any type of medicament that can be counted and dispensed by an automated and semi-automated pharmacy system including, but not limited to, capsules, tablets, caplets, gel caps, lozenges, and the like.

The term "wizard", as used herein, refers to a computer utility designed to simplify the execution of lengthy or complicated tasks. As known to those of skill in the art, a wizard is essentially a programmatic method of providing guidance to a user via GUIs.

The present invention may be embodied as systems, methods, and/or computer program products for carrying out various operations of an automated pharmacy machine. Accordingly, the present invention may be embodied in hardware and/or in software (including firmware, resident software, micro-code, etc.). Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example, but not limited to, an electronic, magnetic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), and a portable compact disc read-only memory (CD-ROM).

The present invention is described herein with reference to graphical user interfaces (GUIs), flowchart illustrations and block diagram illustrations of methods, systems, and computer program products for implementing the various operations of an automated pharmacy machine, according to embodiments of the present invention. It will be understood that each block of the flowchart and/or block diagram illustrations, and combinations of blocks in the flowchart and/or block diagram illustrations, may be implemented by computer program instructions and/or hardware operations. These computer program instructions are provided to a processor, or other programmable data processing apparatus to produce a machine, such that the instructions, which execute via the processor and create means for implementing the functions specified in the GUIs, flowcharts and block diagram blocks.

These computer program instructions may also be stored in a computer usable or computer-readable memory such that the instructions produce an article of manufacture including instructions that implement the functions specified in the GUIs, flowcharts and block diagram block.

The computer program instructions may also be loaded onto a controller or other programmable data processing apparatus to cause a series of operational steps to be performed on the controller or other programmable apparatus to produce a computer implemented process such that the instructions that execute on the controller or other programmable apparatus provide steps for implementing the functions specified in the GUIs, flowcharts, and block diagram blocks.

Referring to FIG. 1, an exemplary process of an automated pharmacy machine for processing a prescription, according to some embodiments of the present invention, is described. The process begins with the identification of the proper container (i.e., a vial that will be used to contain the medicine), tablets or capsules and closure to be dispensed based on a patient's prescription information (Block 20). A container of the proper size is dispensed at a container dispensing station (Block 22), then moved to a labeling station (Block 24). A printing station prints a label (Block 25) that is applied to the container at the labeling station (Block 26), after which the labeled container is transferred to a tablet dispensing station (Block 28), from which the designated tablets are dispensed in the designated amount into the container (Block 30). The filled container is then moved to a closure dispensing station (Block 32), where a closure of the proper size has been dispensed (Block 34). The filled container is secured with a closure (Block 36), then transported to an offload station and offloaded (Block 38).

Figure 2:
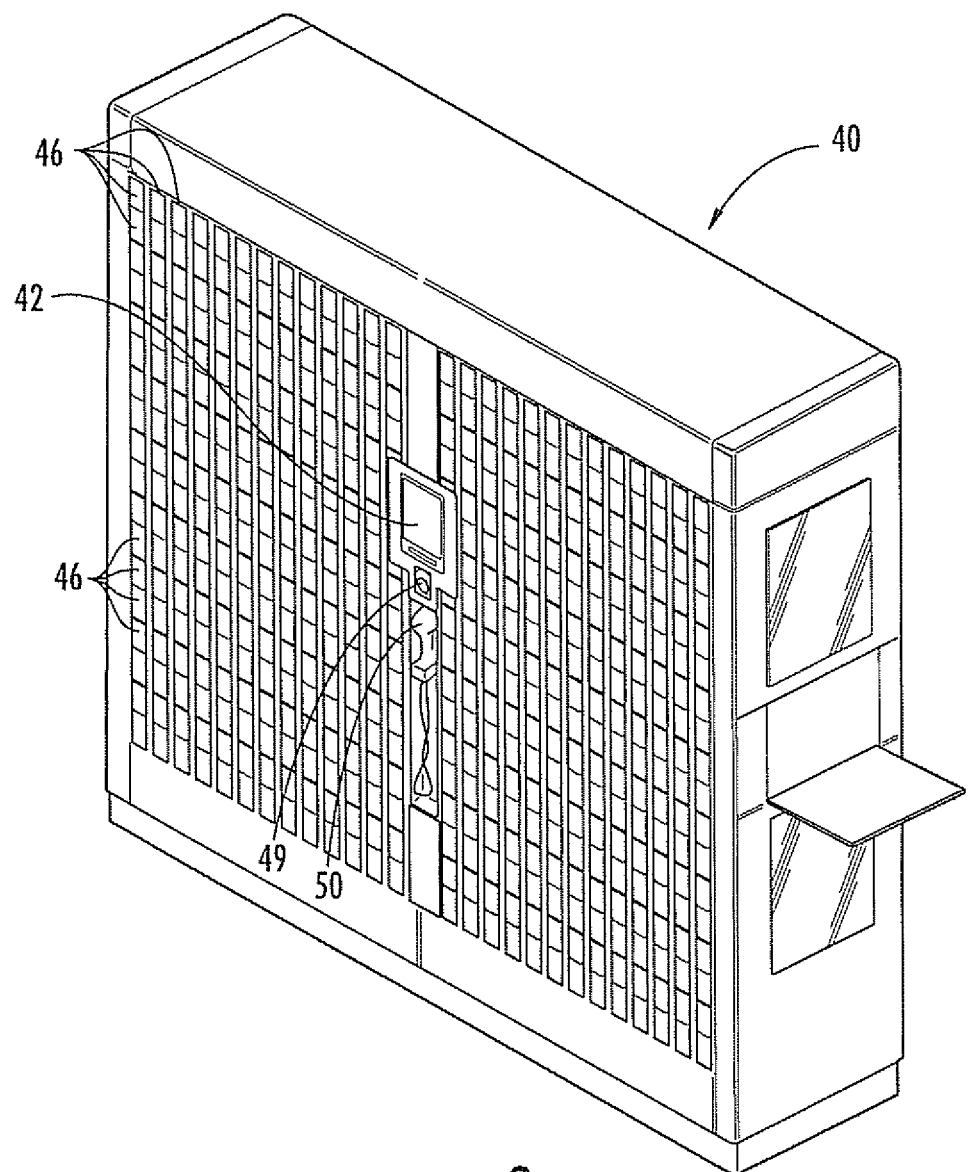
FIG. 2 is a front perspective view of a pharmaceutical dispensing system according to embodiments of the present invention.
Figure 3:
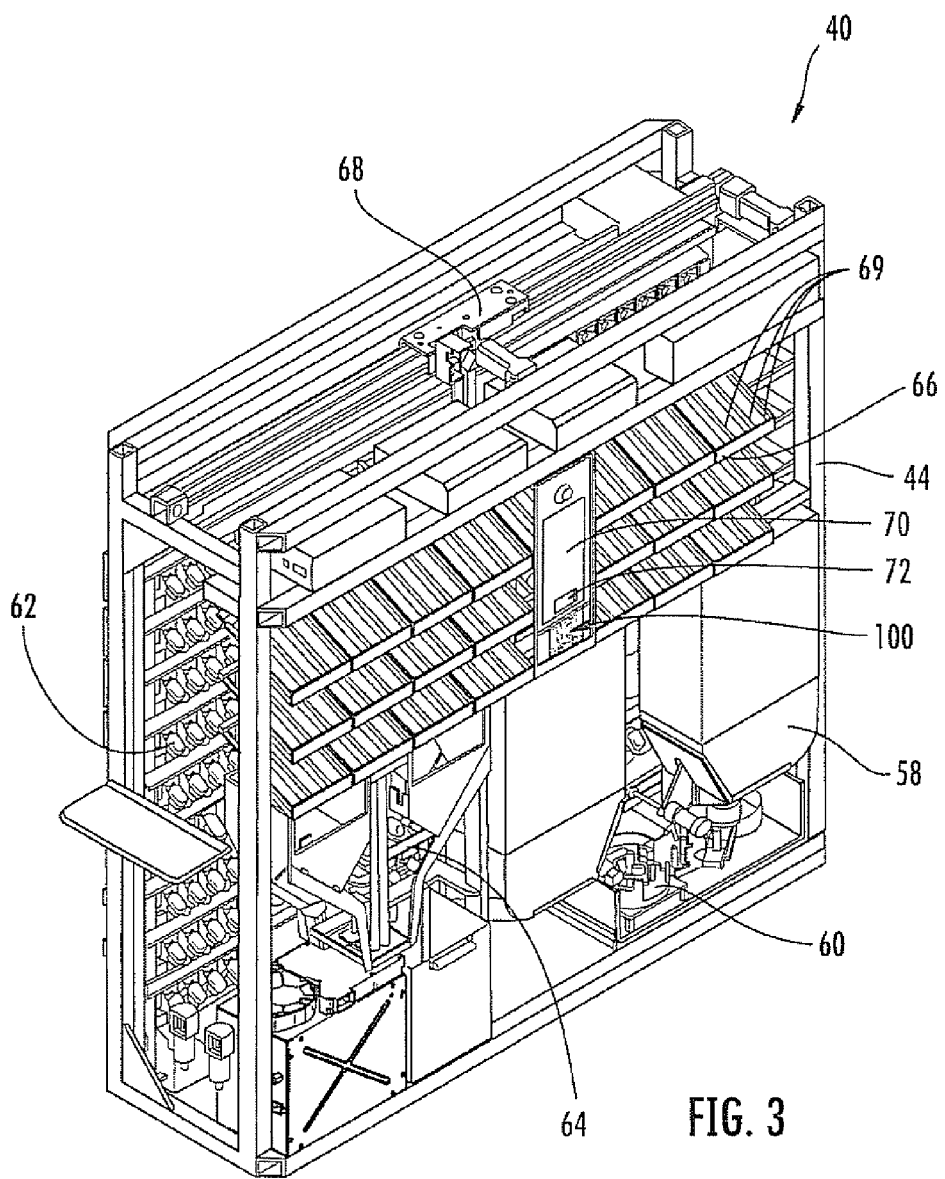
FIG. 3 is an opposite side front perspective view of the pharmaceutical dispensing system of FIG. 2 with the outer skin removed to permit visual access to components housed therein.

A system that can carry out this process is illustrated in FIGS. 2 and 3 and is designated broadly therein at 40. The system 40 includes a support frame 44 for the mounting of its various components. The system 40 generally includes as operative stations a controller (represented in FIGS. 2 and 3 by graphics user interface monitors 42 and 70), a container dispensing station 58, a labeling station 60, a tablet dispensing station 62, a closure station 64, and an offloading station 66 including a plurality of bins or shelves 69. In the illustrated embodiment, containers, tablets and closures are moved between these stations with a single carrier or robotic arm 68; however, in some embodiments additional carriers/robotic arms may be employed. The operation of the container dispensing station 58, the labeling station 60, the tablet dispensing station 62, and the closure station 64, and the offloading station 66 are described in, for example, U.S. patent application Ser. Nos. 11/599,526; 11/599,576; 11/679,850; 11/693,929; 11/755,249; 11/927,865; and 11/111,270, the disclosure of each is incorporated herein in its entirety.

According to some embodiments of the present invention, monitors 42 and 70 are touch screen monitors that display graphical user interfaces (GUIs) that allow operators to perform various functions. For example, an operator interacts with graphical representations (e.g., application icons) and controls (e.g., buttons, scroll bars, etc.) collectively referred to herein as GUI controls. These GUI controls perform various functions in response to physical touching by an operator (e.g., touching or tapping via a finger or stylus). GUIs displayed on each side of the pharmaceutical dispensing system 40 relate to tasks that can be performed on the respective sides of the pharmaceutical dispensing system 40. For example, an operator monitors and controls the filling of prescriptions by interacting with GUI controls displayed via the dispensing side monitor 70. An operator performs cell replenishment operations by interacting with GUI controls displayed via the replenishing side monitor 42.

Although the pharmaceutical dispensing system 40 employs robotic automation to fill prescription orders, the system 40 still requires a certain amount of operator monitoring and management. An operator monitors the pharmaceutical dispensing system 40 and interacts with it when initiating certain functions and procedures, e.g., replenishing a counting cell 46, processing a manual prescription fill, etc. According to some embodiments of the present invention, the various GUIs share a common set of functional GUI controls. Moreover, all GUI windows and screens are labeled and employ a consistent "look and feel." In addition, GUI controls related to routine prescription queue management activities are color-keyed and informative. Some GUI controls appear on all toolbars and wizards displayed within the various GUIs. Other GUI controls are context-sensitive.

Instead of employing physical input devices, such as a keyboard, numeric keypad, or mouse, the various GUIs display a virtual keyboard/keypad when one is needed. The operator's finger, in effect, replaces the mouse. According to embodiments of the present invention, the virtual keyboard displayed in various ones of the GUIs includes a filtering function, as will be described below.

The side of the system 40 illustrated in FIG. 2 is referred to as the "inventory side" or "replenishing side." The replenishing side of the system 40 includes an array of cells 46, each of which is configured to store pills of a respective drug. The replenishing side of the system 40 also includes barcode scanners 49, 50 for scanning barcodes associated with cells 46 and containers. The system 40 dispenses pills from a cell to fill a particular prescription. GUIs displayed via the monitor 42 on the replenishing side are configured to display various types of information to an operator regarding the status of pill inventory in the various cells 46. In addition, various operator tasks may be performed via GUIs displayed via the replenishing side monitor 42 including, but not limited to, operations associated with replenishing cells 46 with pills, adding a new drug to inventory, setting up parameters of a cell 46, modifying parameters of cells 46, and performing return-to-stock (RTS) operations, each of which will be described below.

The side of the system 40 illustrated in FIG. 3 is referred to as the "prescription side" or the "dispensing side." The monitor 70 on the dispensing side displays, via various GUIs, information to an operator regarding the status of prescription filling operations (e.g., pending, complete, incomplete, etc.). If a prescription filling operation cannot be completed for some reason, a GUI displays relevant information regarding this via monitor 70. In addition, various operator tasks may be performed via GUIs displayed via the dispensing side monitor 70 including, but not limited to, prescription order monitoring/processing, performing manual prescription filling, scanning out completed prescriptions, resubmitting exceptions, and performing system operations (e.g., homing/parking the robotic arm 68, configuring cells 46, running diagnostics, etc.), each of which will be described below.

Dispensing Side GUIs

Prescription processing is monitored and managed from the dispensing side of the system 40. An operator monitors and controls the filling of prescription orders by touching various GUI controls in the GUIs displayed on the dispensing side monitor 70. Dispensing side tasks include prescription order monitoring/processing, performing manual prescription fills, scanning out completed prescriptions, resubmitting exceptions, and performing routine system operations (e.g., homing/parking the robotic arm 68, configuring cells 46, running diagnostics, etc.).

Figure 4:
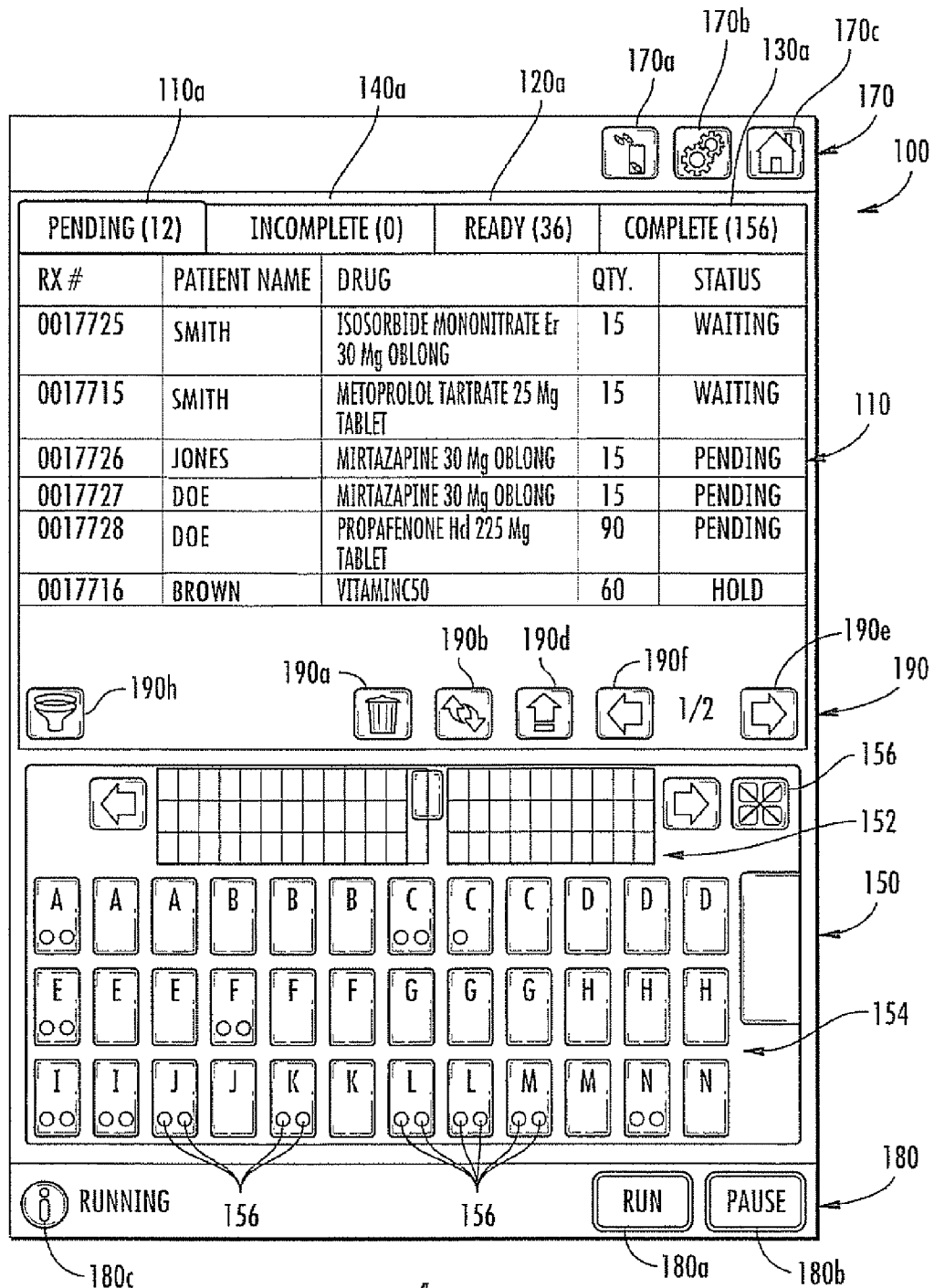
FIGS. 4-12; 13A-13E; 14A-14C; 15A-15F; and 16A-16C are graphical user interfaces (GUIs) that allow an operator of the pharmaceutical dispensing system of FIGS. 2-3 to perform various functions, in accordance with various embodiments of the present invention.

A Home GUI 100, illustrated in FIG. 4, is utilized for prescription monitoring and prescription queue management activities. An upper portion of the Home GUI 100 displays prescription orders that have been transmitted from a pharmacy's computer to the system 40. The Home GUI 100 displays a series of GUIs, wherein each GUI in the series comprises status information about a prescription order at a respective stage of completion of the prescription order by the pharmaceutical dispensing system 40. The series of GUIs includes a Pending Queue GUI 110 (FIG. 4), a Ready Queue GUI 120 (FIG. 5), a Complete Queue GUI 130 (FIG. 6), and an Incomplete Queue GUI 140 (FIG. 7). Each of these GUIs includes a tab that, when touched by an operator, displays the respective GUI within the Home GUI 100. For example, the Pending Queue GUI 110 includes tab 110*a*, the Ready Queue GUI 120 includes tab 120*a*, a Complete Queue GUI 130 includes tab 130*a*, and the Incomplete Queue GUI 140 includes tab 140*a*.

The number of prescription orders in each of the various GUIs 110-140 appears in the respective tab 110*a*-140*a* associated therewith. For example, in the illustrated embodiment of FIG. 4, there are twelve (12) pending prescription orders, zero (0) incomplete prescription orders, thirty-six (36) ready prescription orders, and one hundred fifty six (156) complete prescription orders. Touching each of the columns in the queue of each of the GUIs 110-140 sorts the items in that column (ascending/descending). In addition, an operator can filter the ready queue to display all prescription orders for a particular patient by touching Filter GUI control 190*h*.

The Pending Queue GUI 110 displays all prescription orders coming into the system 40 for filling. For example, the Pending Queue GUI 110 displays prescription orders that have been transmitted by a pharmacy computer system to the pharmaceutical dispensing system 40 and/or that have been entered into the pharmaceutical dispensing system 40 manually by an operator. The Ready Queue GUI 120 displays all prescription orders that have been successfully filled and that are ready for pickup. The Incomplete Queue GUI 140 displays all prescription orders that, for whatever reason, were not successfully filled (i.e., exception prescription orders, etc.). The Complete Queue GUI 130 displays all prescription orders that have been filled and picked up, as well as prescription orders that have been deleted, canceled or cleared from the prescription drop-off or dispensing shelves 69. The Home GUI 100 allows an operator to easily display prescription orders that are pending, incomplete, ready and complete by selecting the appropriate tab 110*a*-140*a*.

As each prescription order is processed by the pharmaceutical dispensing system 40, a pill container (i.e., vial) is labeled, filled, capped, and then deposited in a dispensing shelf 69 (FIG. 3), usually by the patient's last name. The processed prescription order automatically appears in the Ready Queue GUI 120, illustrated in FIG. 5, and is automatically removed from the Pending Queue GUI 110. The Ready Queue GUI 120 identifies the location (i.e., the dispensing shelf 69) of the filled pill container. For example, in the illustrated embodiment, the information displayed in the Ready Queue GUI 120 includes prescription number, patient name, drug, quantity, and location. An operator locates the dispensing shelf 69 containing the filled container, removes the container therefrom, and scans the bar code on the container label via a scanner 72 associated with the pharmaceutical dispensing system 40.

Figure 5:
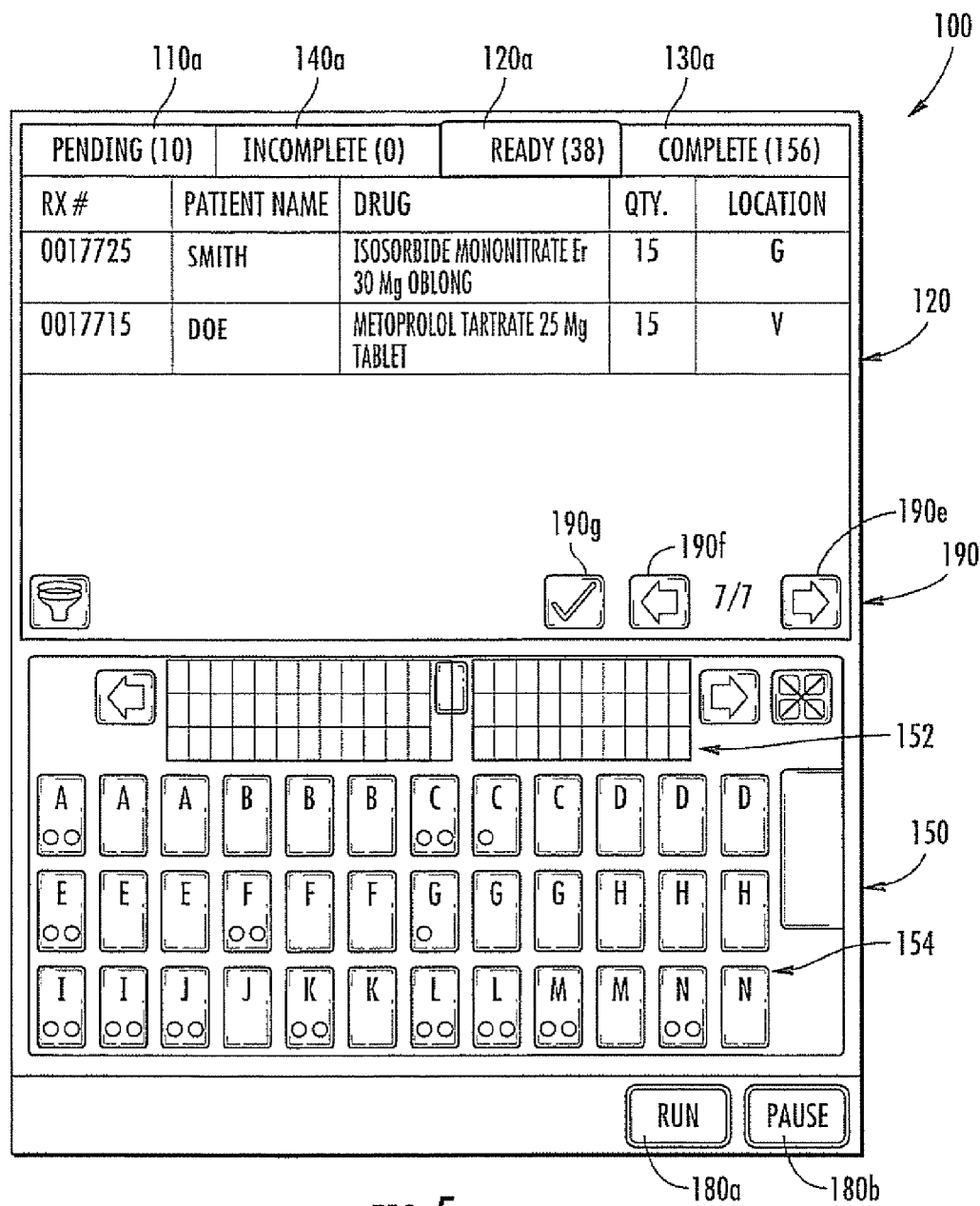
Figure 6:
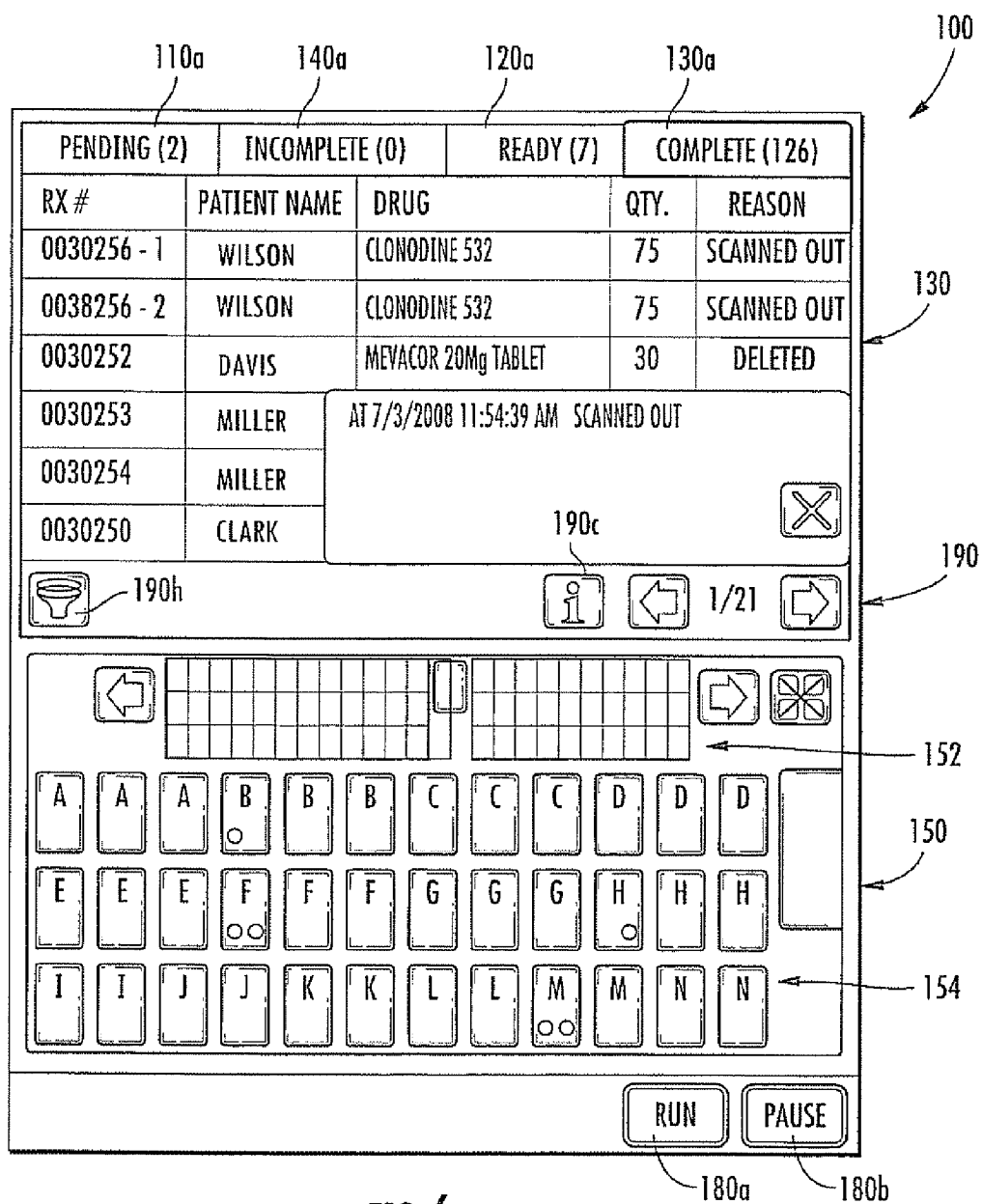
Figure 7:
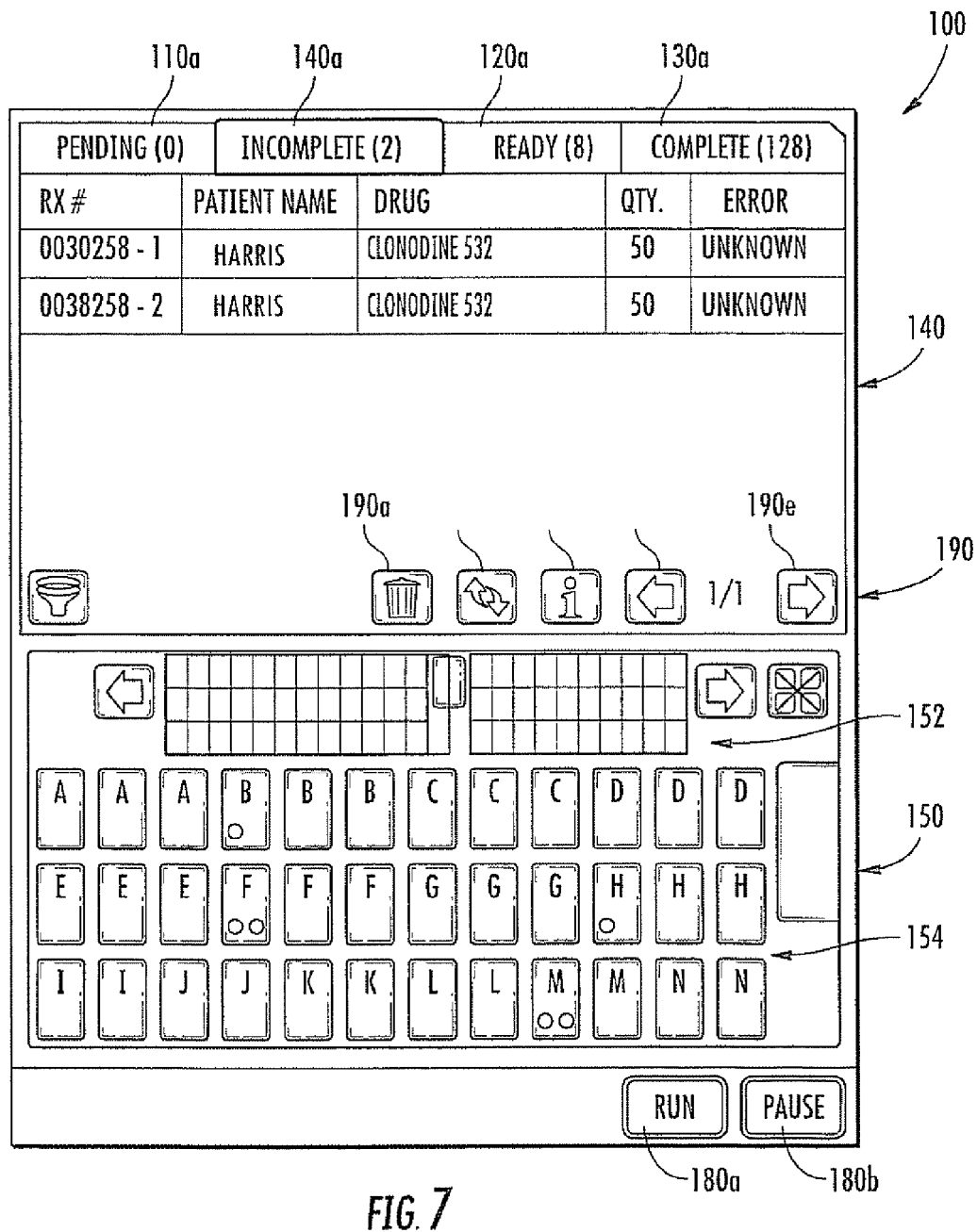

Scanning a container's bar code, for example via scanner 72, transfers a prescription from the Ready Queue GUI 120 (FIG. 5) to the Complete Queue GUI 130 (FIG. 6). The Complete Queue GUI 130 lists all completed prescription orders that have been processed by the system 40, as well as orders deleted, cancelled, or cleared from the dispensing shelves 69. The illustrated Complete Queue GUI 130 displays the following information: prescription number, patient name, drug, quantity, and reason for the prescription order being designated as "complete."

Incomplete prescription orders are displayed in the Incomplete Queue GUI 140 (FIG. 7). The illustrated incomplete Queue GUI 140 displays the following information: prescription number, patient name, drug, quantity, and error (i.e., the reason for the prescription order being designated as "incomplete"). Causes for incomplete prescription orders include, but are not limited to, insufficient pill inventory, malfunctioning containers, malfunctioning labels, prescription orders that were not filled, capped or labeled correctly, or that were cancelled, etc. When an operator selects a prescription order displayed in the Incomplete Queue GUI 140 and then activates GUI control 190*c* (FIG. 6), the reason that the selected prescription order is incomplete appears in a pop-up window.

A lower portion of the Home GUI 100 displays the Ready Shelf GUI 150 that is a graphical representation of the dispensing shelves 69 and prescription orders that are ready and that await pickup therefrom. In the illustrated embodiment, the Ready Shelf GUI 150 is displayed within the Home GUI 100 when each of the above-described GUIs are displayed in the upper portion of the Home GUI 100, i.e., the Pending Queue GUI 110, the Ready Queue GUI 120, the Complete Queue GUI 130, and the Incomplete Queue GUI 140. Via the Ready Shelf GUI 150, an operator can perform various functions including clear individual prescription dispensing shelves 69, clear all dispensing shelves 69, print prescription dispensing shelf labels, and confirm pill container pickup from a dispensing shelf 69.

Figure 8:
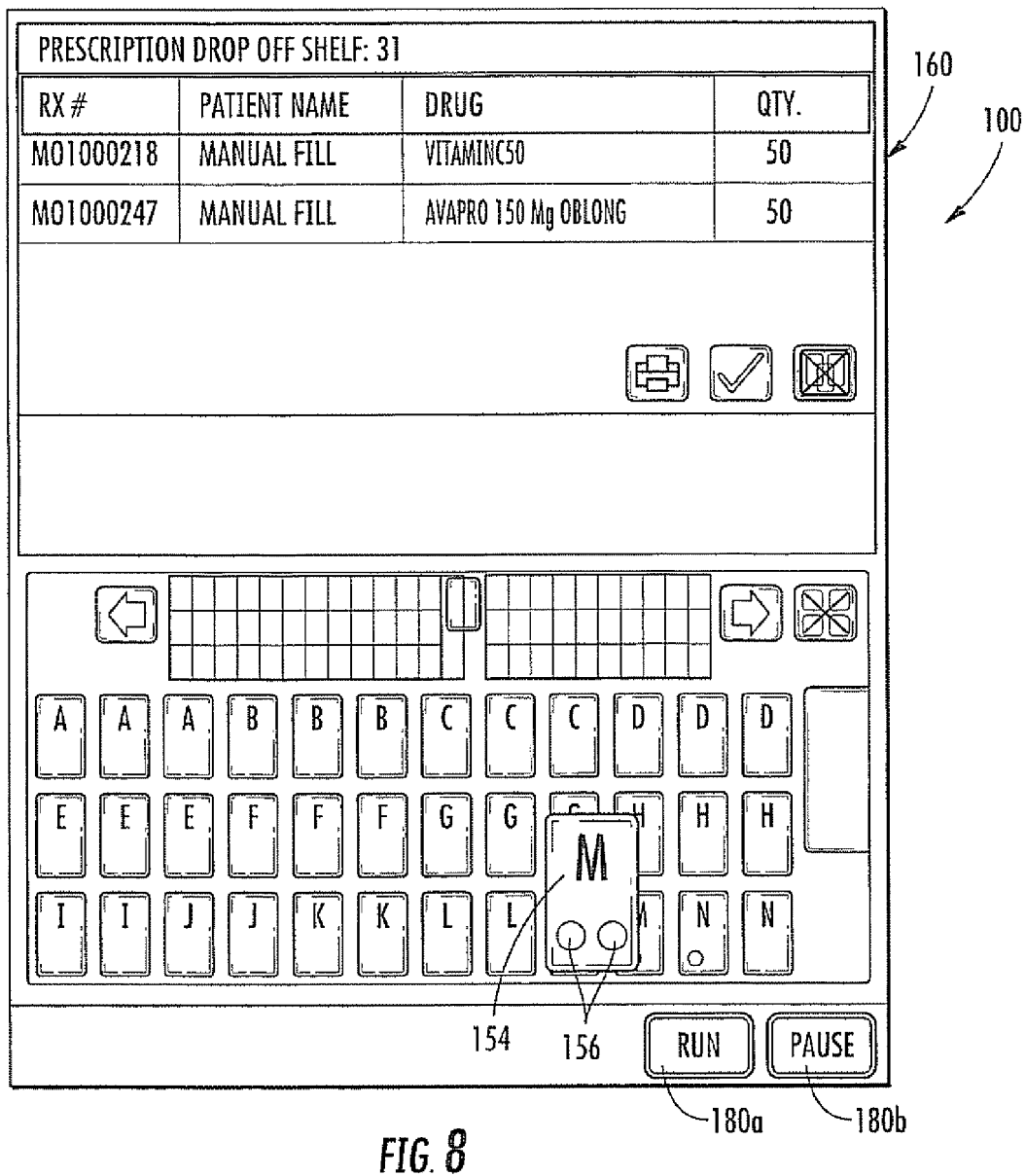

The illustrated Ready Shelf GUI 150 displays a graphical representation 152 of the array of dispensing shelves 69 of the pharmaceutical dispensing system 40. Below the array representation 152 is an array of icons 154, each identified by a letter and each associated with a respective dispensing shelf 69. Dots 156 in the various icons 154 indicate the number of prescription orders that are currently in dispensing shelves 69 awaiting pickup. Each icon 154 represents a respective dispensing shelf 69 of the pharmaceutical system 40. The contents of a respective dispensing shelf 69 are displayed within a Shelf Contents GUI 160 located in the upper portion of the Home GUI 100, in response to an operator touching the corresponding icon ("M") 154, as illustrated in FIG. 8. The illustrated Shelf Contents GUI 160 displays the following information: prescription number, patient name, drug, and quantity for each pill container on the respective dispensing shelf 69. Also, as illustrated, the icon 154 includes two dots 156 which represent the number of pill containers in the corresponding dispensing shelf 69. Indicia of other shapes and configurations may be utilized, however. Embodiments of the present invention are not limited to the illustrated dots.

The capacity for each dispensing shelf 69 for the illustrated pharmaceutical dispensing system 40 is two pill containers. As such, each icon in the Ready Shelf GUI 150 will contain either zero dots (i.e., no pill containers in the respective dispensing shelf 69), 1 dot (i.e., one pill container in the respective dispensing shelf 69), or two dots (i.e., two pill containers in the respective dispensing shelf 69). When an operator removes a pill container from a full shelf 69 (i.e., a shelf 69 with two pill containers), a sensor detects that the shelf 69 is no longer full and is available for more pill containers. The pharmaceutical dispensing system 40 tracks the number of pill containers sent to the shelf 69 and determines when more pill containers have been sent than the shelf 69 will hold. When the third pill container is placed on the shelf 69, an Auto-Complete function associated with the Ready Shelf GUI 150 assumes that the oldest pill container has been removed by an operator and the script for that pill container is moved from the Ready queue to the Complete queue. This process will continue until only two pill containers remain on the shelf 69 (the shelf capacity) and there are no others in the queue assigned to that shelf 69.

Referring back to FIG. 4, the Home GUI 100 has an upper main toolbar 170 and a lower main toolbar 180. GUI controls included in the upper main toolbar 170 include Manual Fill GUI control 170a, System Functions GUI control 170b and Home GUI control 170c. Manual Fill GUI control 170a, when touched by an operator, allows the operator to enter a prescription into the system 40 manually (rather than it being sent to the system 40 automatically, such as from a pharmacy host system). Upon activating GUI control 170a, a manual fill wizard is launched that allows an operator to fill a prescription order manually. System Functions GUI control 170b allows an operator to display and/or configure various parameters of the pharmaceutical dispensing system 40. Home GUI control 170c, when touched by an operator, displays the Home GUI 100.

GUI controls included in the lower main toolbar 180 include Run GUI control 180a, Pause GUI control 180b, and Open Message Queue GUI control 180c. A user touches the Run GUI control 180a to process and fill prescription orders. In "Run" mode, pending prescription orders are filled. A user touches the Pause GUI control 180b to suspend prescription order processing. In "Pause" mode, prescription orders can be submitted to the pharmaceutical dispensing system 40, but are not filled until the Run GUI control 180a is touched. The Open Message Queue GUI control 180c, when touched by a user, opens the alert message queue. Open Message Queue GUI control 180c is displayed automatically when there is a message. The alert message queue contains messages generated by the pharmaceutical dispensing system 40, for example, error messages that relate to system-level problems such as with filling prescriptions, etc. Touching the Open Message Queue GUI control 180c displays a list of the most recent alert messages (e.g., up to five, etc.) issued by the pharmaceutical dispensing system 40.

The illustrated Home GUI 100 also has a taskbar 190 containing context-sensitive GUI controls. GUI controls are enabled only when their functions can be performed via the currently displayed queue GUI (e.g., Pending Queue GUI 110, Ready Queue GUI 120, Complete Queue GUI 130, Incomplete Queue GUI 140). Delete GUI control 190a deletes a selected prescription order. For example, to delete or cancel a pending prescription order from the pending queue, an operator selects a pending prescription order in the Pending Queue GUI 110 and then touches GUI control 190a to delete the prescription.

Retry GUI control 190b resubmits a prescription order. This is used mainly to retry running/waiting prescription orders. In operation, a prescription order displayed in the Pending Queue GUI 110 is selected. The operator then touches GUI control 190b to resubmit the selected prescription order for processing.

Details GUI control 190c (FIG. 6) displays detail information about incomplete (and complete) prescription orders. Advance GUI control 190d moves a prescription order to the top of its queue. For example, a prescription order displayed within Pending Queue GUI 110 is selected. An operator then touches GUI control 190d to advance this prescription order to the top of the displayed queue.

Next/Last GUI controls 190e, 190f allow an operator to move forward and backward, respectively, through multiple pages of displayed information.

During automated prescription order processing via the pharmaceutical dispensing system 40, an operator monitors and manages the prescription order processing via the Home GUI 100. In the Pending Queue GUI 110, pending prescription orders are displayed. In other words, prescription orders sent to the pharmaceutical dispensing system 40 from a pharmacy computer are displayed within Pending Queue GUI 110. If the pharmaceutical dispensing system 40 is not in "Run" mode, the operator touches the Run GUI control 180a. As each prescription order is processed, it is labeled, filled, capped, and deposited in a prescription dispensing shelf 69, customarily by the patient's last name.

In FIG. 4, the illustrated Pending Queue GUI 110 displays a list of prescription orders that have been sent to the pharmaceutical dispensing system 40. The first two records correspond to two prescription orders that have been filled and for which the pill containers are currently waiting in respective dispensing shelves 69. For these two prescription orders, an operator touches the Ready Queue GUI tab 120c and the prescription orders that are ready to be picked up are displayed within the Ready Queue GUI 120 of FIG. 5. The Ready Queue GUI 120 in FIG. 5 lists all prescription orders that have been successfully processed and are ready to be picked up from the dispensing shelves 69. The dispensing shelf locations appear in the last column entitled "Location."

To complete a prescription order, an operator locates the prescription dispensing shelf 69 containing a prescription, removes the pill container from the dispensing shelf 69 and scans the bar code on the pill container label via bar code scanner 72. Instead of scanning out the pill container, the operator could alternatively pick up the pill container from the prescription dispensing shelf 69, select the prescription order from the Ready queue GUI 120 (FIG. 5), and touch the Complete GUI control 190g in the taskbar 190. A confirmation window may also be displayed in response to touching the Complete GUI control 190g for the purpose of requiring the operator to verify that he/she intended for a particular prescription order to be indicated as being complete. Alternatively, an operator can wait until all pending prescription orders have been successfully run and then clear them all at once, or one dispensing shelf 69 at a time, from the Ready Queue GUI 120. This is done by the operator touching the Clear All Shelves GUI control 156 within the Ready Shelf GUI 150.

Replenishing Side GUIs

Figure 9:
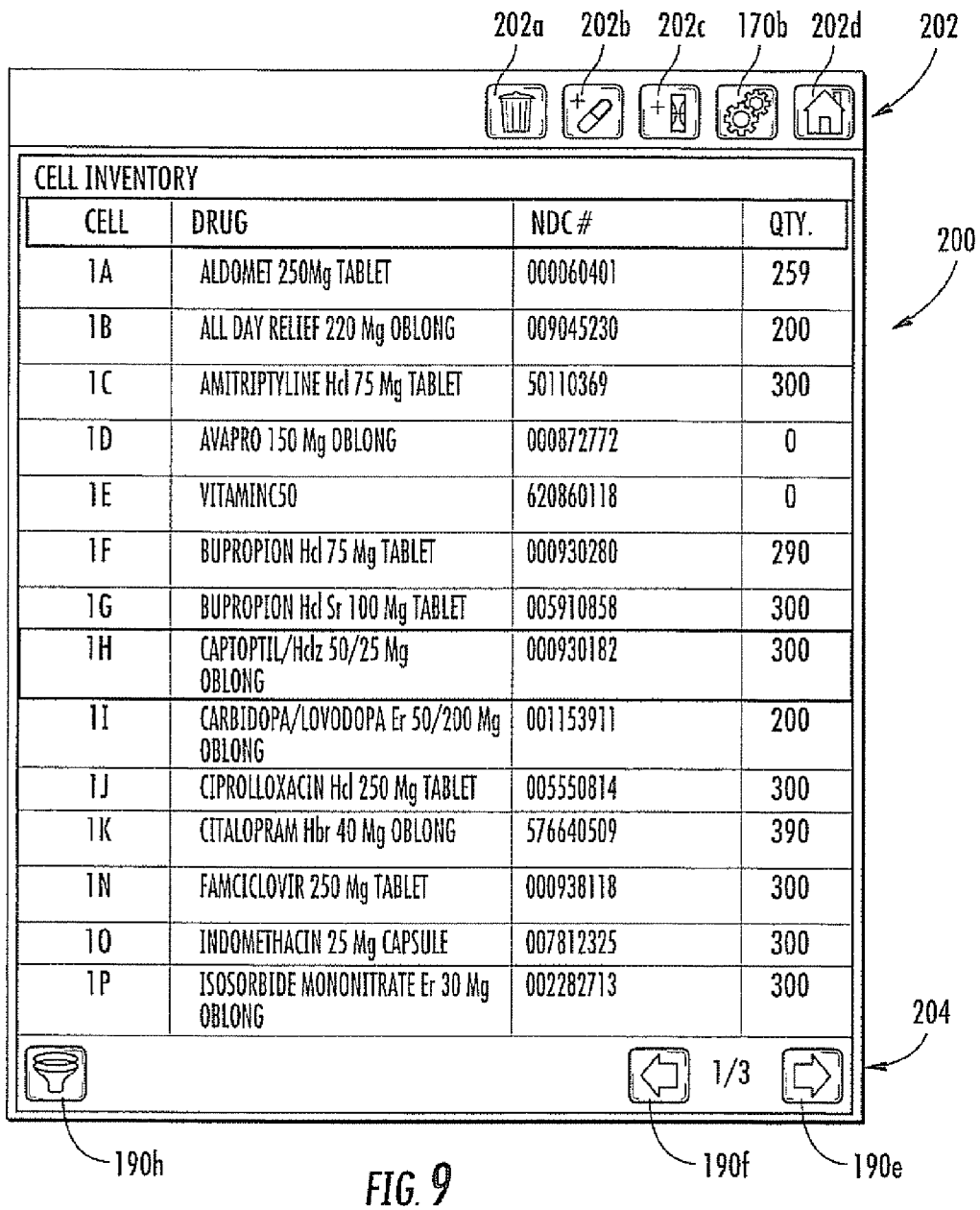

Referring now to FIG. 9, a Cell Inventory GUI 200 is illustrated. The Cell Inventory GUI 200 is considered the "Home GUI" for the replenishing side of the pharmaceutical dispensing system 40. The Cell Inventory GUI 200 displays information about the contents of cells 46 on the replenishing side of the pharmaceutical dispensing system 40 that are currently calibrated to contain a particular drug. For example, the Cell Inventory GUI 200 displays the following information about each cell 46: cell location, drug contained within cell, NDC (National Drug Code) information, and drug quantity in each cell. As known to those skilled in the art, drug products are identified and reported using a unique, three-segment NDC number, which is a universal product identifier for human drugs.

The illustrated Cell Inventory GUI 200 has an upper main toolbar 202 and a lower main toolbar 204. GUI controls in the upper main toolbar 202 include Delete Cell GUI control 202a, New Drug GUI control 202b, New Cell GUI control 202c, Systems Functions GUI control 170b, and Home GUI control 202d. Systems Functions GUI control 170b is the same GUI control as described above with respect to the Home GUI 100 of FIG. 4. The Delete Cell GUI control 202a allows an operator to delete a cell 46 from a database of the pharmaceutical dispensing system 40.

The Cell Inventory GUI 200 serves as the launching point for various wizards, including a Replenish wizard, an RTS wizard, a New Cell wizard, and a New Drug wizard, etc. The wizard GUI controls appear in the upper main toolbar 202. For example, the New Drug GUI control 202b launches a New Drug wizard that is used by an operator when adding a new drug to the inventory of the pharmaceutical dispensing system 40, as will be described below. The New Cell GUI control 202c launches a New Cell wizard that is used by an operator when setting up a new cell 46, as will be described below. The Home GUI control 202d displays the Cell Inventory GUI 200.

Figure 12:
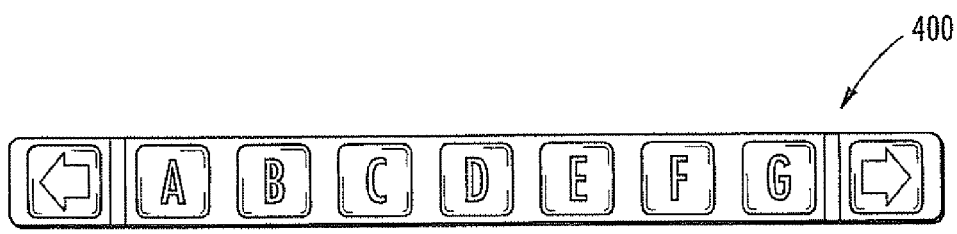
Figure 13A:
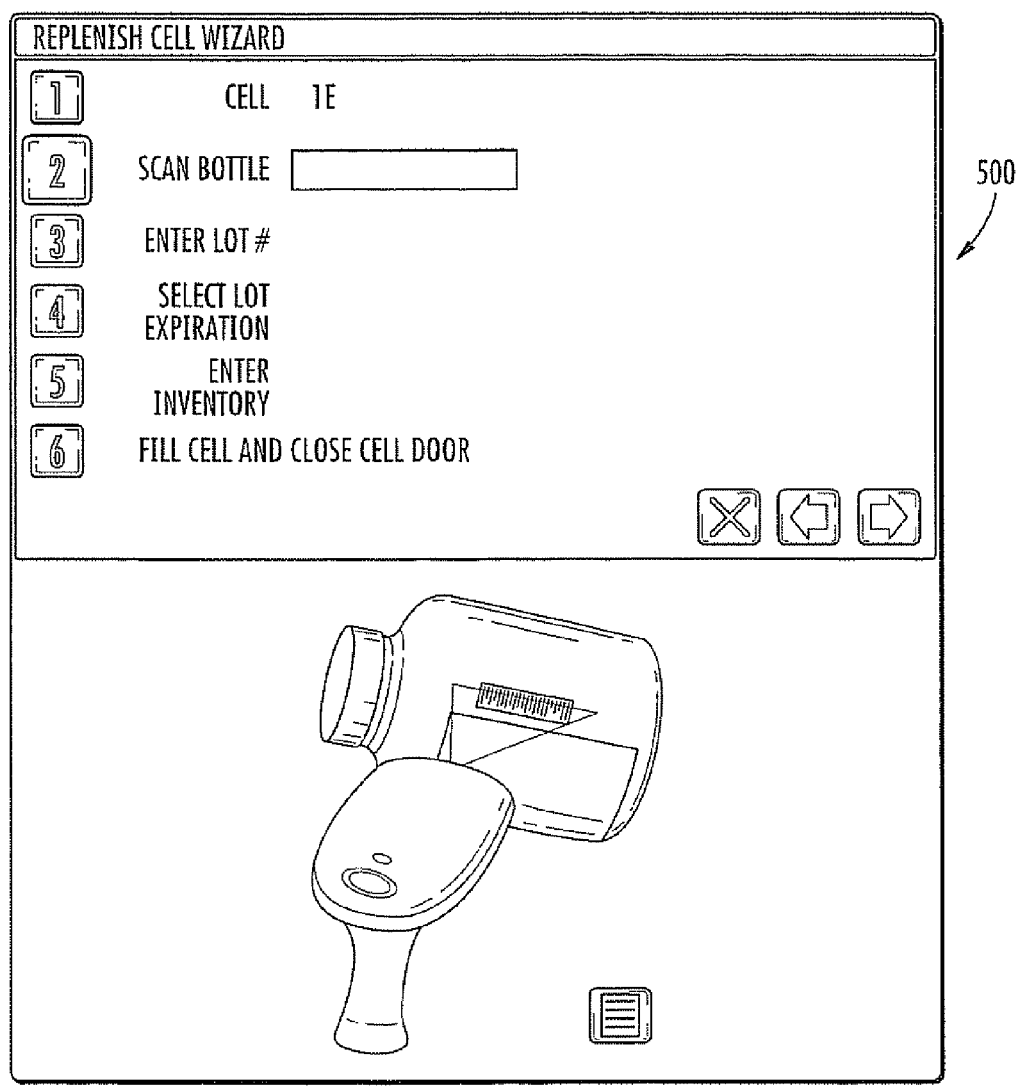
Figure 13B:
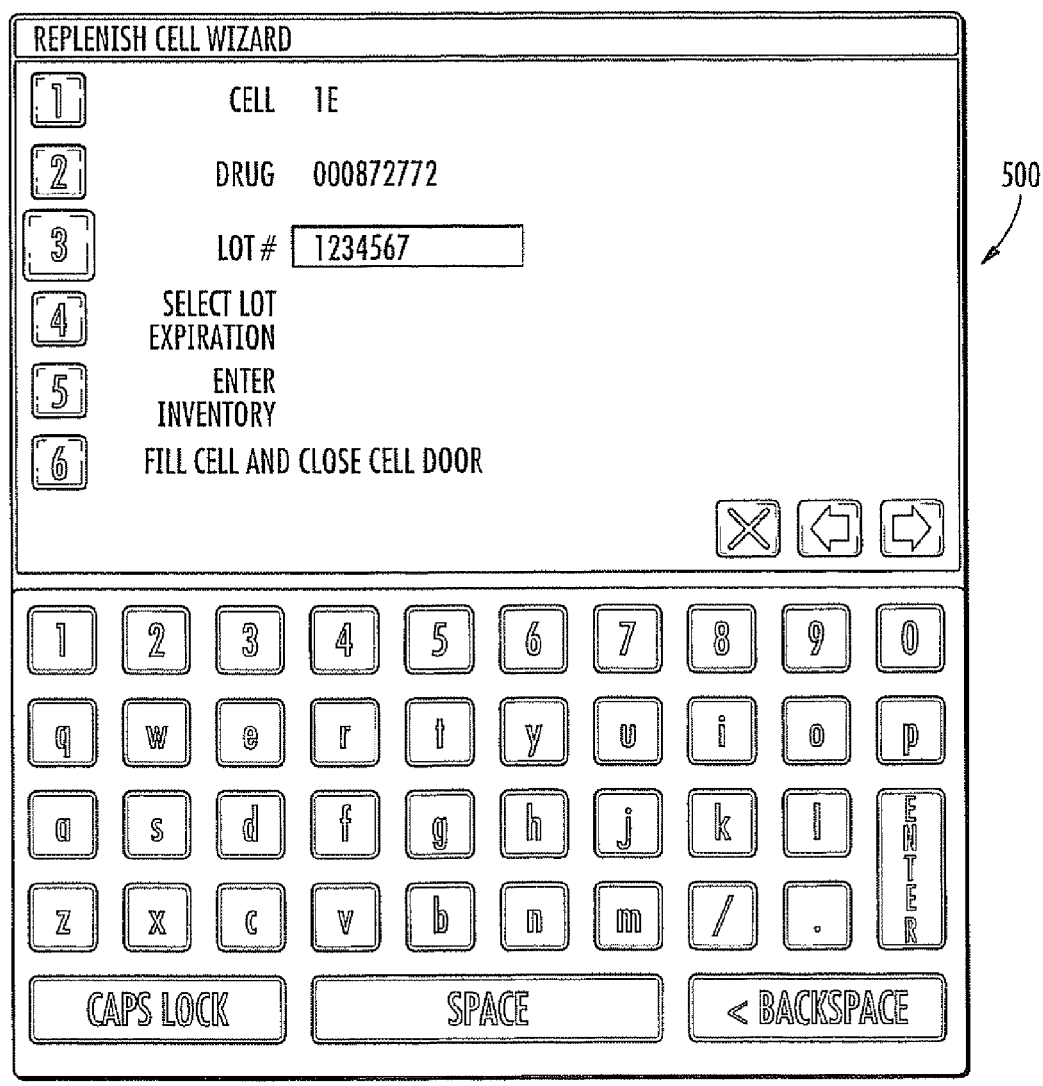
Figure 13C:
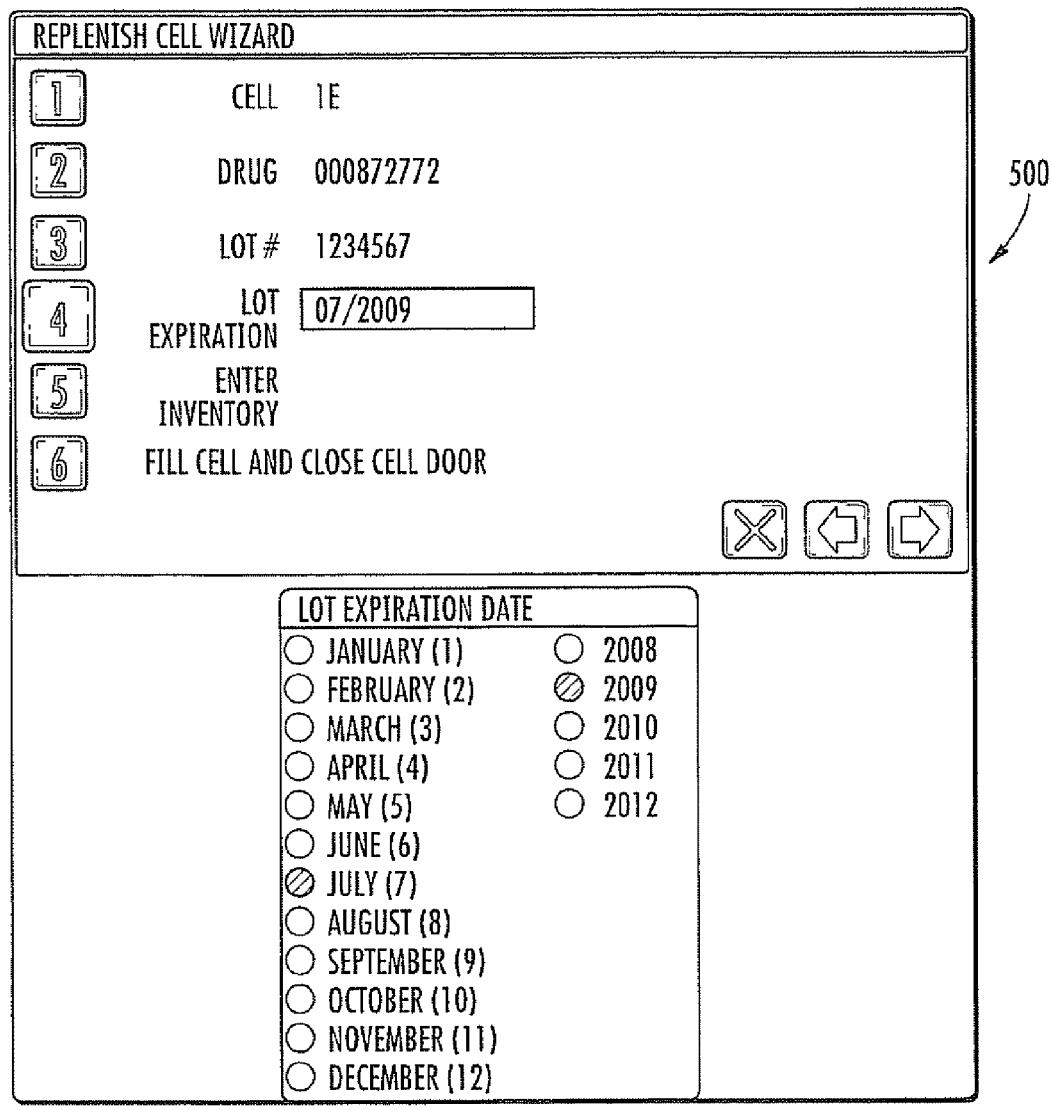
Figure 13E:
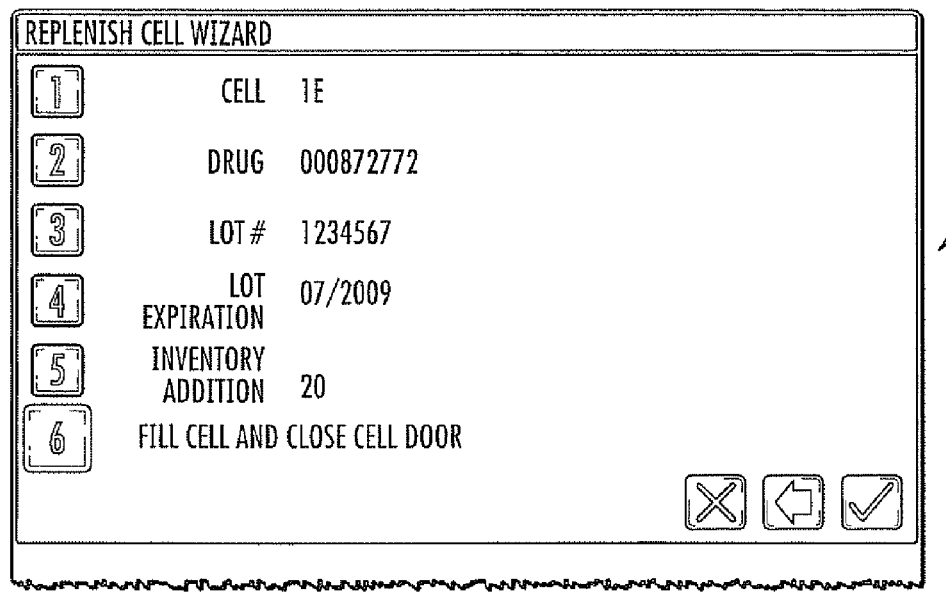

GUI controls in the lower main toolbar 204 include the Filter GUI control 190h and Next/Last GUI controls 190e, 190f. As described above, Filter GUI control 190h allows an operator to filter displayed information via the filter keyboard 400 (FIG. 12). Next/Last GUI controls 190e, 190f allow an operator to move forward and backward, respectively, through multiple pages of displayed information.

The Cell Inventory GUI 200 displays cell inventory information in read-only mode. The displayed information can be filtered and/or sorted. For example, only cells containing a certain drug can be displayed, etc.

In the Cell Inventory GUI 200, cells that are either empty or contain pills below a "low Inventory" level (e.g., less than 50 pills, etc.) are shaded, for example in yellow, so that they are brought to the attention of the operator. Each cell 46 of the pharmaceutical dispensing system 40 includes a status indicator, such as light emitting diode (LED). Touching any row displayed in the Cell Inventory GUI 200 causes the status indicator for the corresponding cell 46 to flash for a predetermined duration, for example 15 seconds. The status indicator allows the operator to quickly locate the cell 46 on the replenishing side of the system 40. Scanning a pill container or stock bottle on the replenishing side of the pharmaceutical dispensing system 40 displays the location of the cell containing the corresponding drug.

Figure 10:
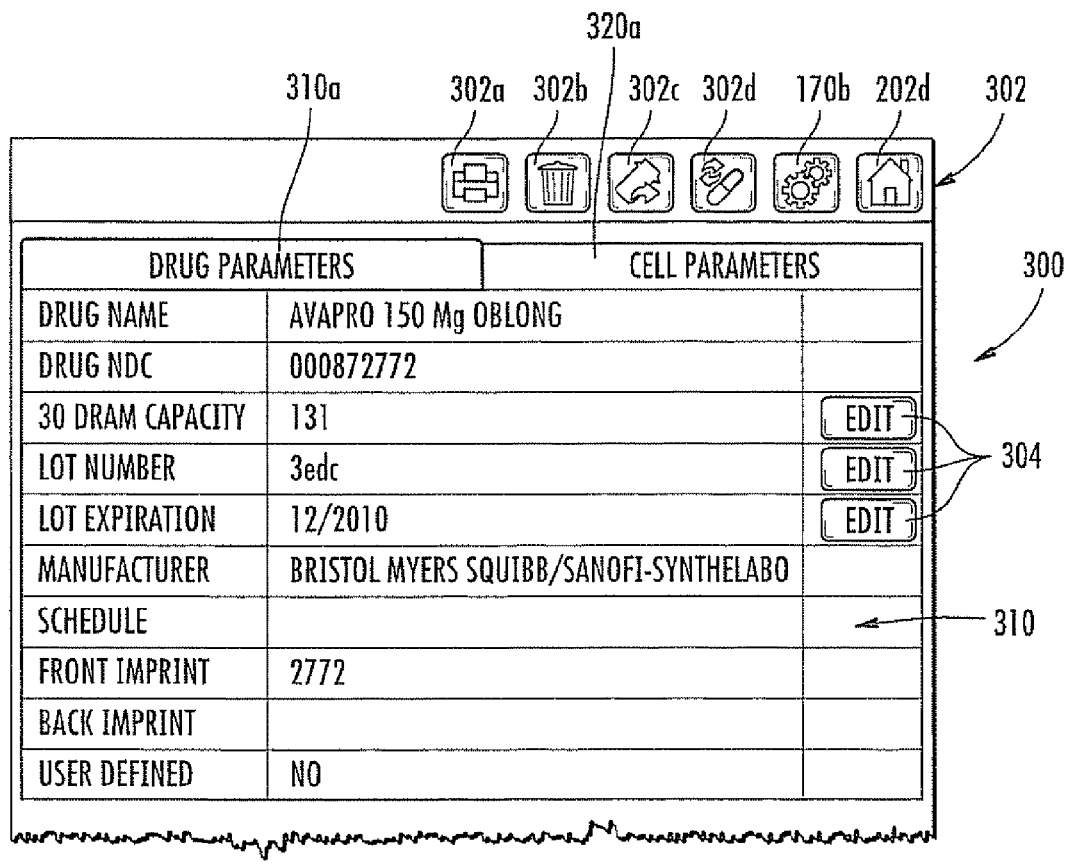
Figure 11:
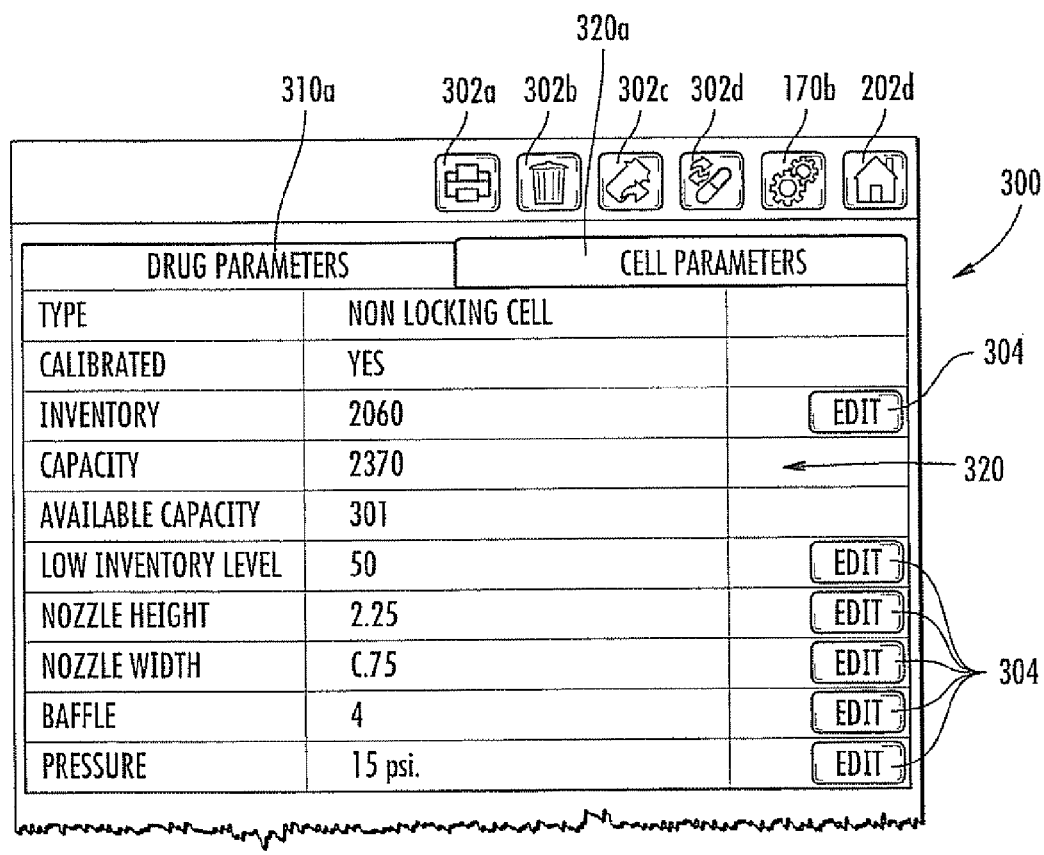

Referring to FIG. 10, a Parameters GUI 300 is illustrated that displays information about a particular cell 46 and a drug contained within the cell 46. The Parameters GUI 300 is configured to display a Drug Parameters GUI 310 and a Cell Parameters GUI 320 (FIG. 11). Drug Parameters GUI 310 is displayed by an operator touching Drug Parameters tab 310a, and the Cell Parameters GUI 320 is displayed by an operator touching the Cell Parameters GUI 320a. An operator can add/modify certain drug and cell settings and values (e.g., air pressure, and other dispensing values) via these two GUIs.

The Parameters GUI 300 includes an upper main toolbar 302. GUI controls in the upper main toolbar 302 include Print GUI control 302a, Delete Cell GUI control 302b, Return to Stock (RTS) GUI control 302c, Replenish Cell GUI control 302d, Systems Functions GUI control 170b, and Home GUI control 202d. The Print GUI control 302a allows an operator to print labels for cells 46. The Delete Cell GUI control 302b allows an operator to delete a cell (i.e., the particular cell 46 for which the Parameters GUI 300 is currently displayed) from a cell database of the pharmaceutical dispensing system 40. The RTS GUI control 302c launches an RTS wizard which allows an operator to return dispensed pills to a cell 46. The Replenish Cell GUI control 302d launches a Replenish Cell wizard that allows an operator to restock the pill inventory of a cell 46. The Home GUI control 202d displays the Cell Inventory GUI 200. The Systems Function GUI control 170b is the same GUI control as described above with respect to the Home GUI 100 of FIG. 4.

The Parameters GUI 300 is accessed by scanning a cell (i.e., scanning a barcode attached to a cell 46 via scanner 50). The Parameters GUI 300 displays the current settings for the scanned cell and for the drug the cell is configured to dispense. For example, in the illustrated Drug Parameters GUI 310 displayed in FIG. 10, parameter information displayed about the drug within a specific cell 46 includes drug name, NDC, lot number, lot expiration, manufacturer, and various other information. Some of these parameters can be modified by an operator via an Edit GUI control 304. In the illustrated Cell Parameters GUI 320 (FIG. 11), parameter information displayed about the cell includes type of cell, capacity, low inventory level, and various other information. Some of these parameters can be modified by an operator via an Edit GUI control 304.

Operations via the various GUIs described above will now be described in further detail.

Processing Prescription Orders

Prescription processing is monitored and managed from the dispensing side of the system 40 via the Home GUI 100 (FIG. 4). The Pending Queue GUI 110 displays all prescription orders currently waiting to be processed by the pharmaceutical dispensing system 40. A prescription order's processing status—Pending, Hold, Waiting, Delay, Labeling, Counting, Capping, Dropping Off—appears in the Status column. Prescription orders currently being processed (except for Pending or Hold orders) are highlighted within the Pending Queue GUI 110. Prescription orders are processed according to the order (date and time) in which they were entered into the pharmaceutical dispensing system 40 (i.e., "first in, first out"). However, an operator can move a prescription order to the top of the queue via the Advance GUI control 190d. An operator can also delete a prescription order from the Pending Queue GUI 110 via Delete GUI control 190a.

As each prescription is processed, it is labeled, filled, capped, and then deposited in a dispensing shelf 69, usually by the patient's last name. The prescription then appears in the Ready Queue GUI 120 (FIG. 5). The operator locates the dispensing shelf 69 containing the filled container, removes the container, and scans the barcode on the label via the system scanner 72. Scanning a container's barcode transfers the prescription order from the ready queue to the complete queue.

The Filter GUI control 190h allows an operator to quickly display prescription orders for patients whose surnames match a filtering key. For example, as illustrated in FIG. 12, when an operator touches the Filter GUI control 190h, a filter keypad 400 is displayed. Using the filtering keypad 400, an operator can find specific information (e.g., a drug name, patient surname, etc.) with the fewest number of keystrokes needed to identify and display the information. For example, if an operator wanted to display all prescription orders for patients with surnames beginning with the letter "C", the operator would touch the letter "C" on the filter keypad 400. The Filter GUI control 190h is available for all of the prescription order queue GUIs 110-140.

In some instances, filtering may be performed automatically. For example, when an operator initiates an RTS procedure by scanning a pill container, the information in the Cell Inventory GUI 200 (FIG. 9) is automatically filtered. In other words, the Cell Inventory GUI 200 displays only the record for the cell that dispensed the prescription order.

When a prescription order has been filled by the pharmaceutical dispensing system 40, the prescription order record transfers to the Ready queue. If the prescription order has encountered an exception, its record moves to the Incomplete queue and the pill container is deposited in an exception carousel instead of being delivered to a dispensing shelf 69. The Ready Queue GUI 120 displays all prescription orders that have been successfully filled by the pharmaceutical dispensing system 40 and that are ready for pickup (i.e., in the ready queue) and delivery to a patient. An operator can clear a prescription order from its dispensing shelf 69 from the Ready Queue GUI 120. An operator can touch any column in the Ready Queue GUI 120 to sort the queue by column heading. Also, an operator can filter information in the Ready Queue GUI 120 to display all prescription orders for a particular patient. Once an operator has scanned out a pill container or cleared the dispensing shelf 69 for a prescription order, its record transfers to the complete queue.

The Complete Queue GUI 130 (FIG. 6) lists all prescription orders that have been filled and delivered, as well as orders deleted, cancelled or cleared from the dispensing shelves 69. The Details GUI control 190c displays the date and time a prescription order was scanned out, picked up, or deleted.

The Incomplete Queue GUI 140 (FIG. 7) displays all prescription orders the pharmaceutical dispensing system 40 was unable to complete, whatever the cause. Orders that were canceled, or that were processed but sent to the exception carousel, also appear in the Incomplete Queue GUI 140. When an operator selects a prescription order in the Incomplete Queue GUI 140 and touches the Details GUI control 190c, the reason its status is Incomplete is displayed and, in many cases, recovery steps are provided (see illustration). The Retry GUI control 190b resubmits a selected prescription order to the pending queue for processing.

Replenish Wizard

There are several occasions when an operator needs to add drugs to one or more of the cells 46. For example, a cell 46 that is empty or whose pill inventory is low needs to be replenished. In addition, when a new drug is added to the pharmaceutical dispensing system 40 one or more cells 46 need to be replenished. Cell replenishment is performed from the replenishing side of the pharmaceutical dispensing system 40. Drug replenishment can occur at any time, including when the pharmaceutical dispensing system 40 is in run mode and processing prescription orders.

The Replenish wizard 500 is illustrated in FIGS. 13A-13E and is launched via Replenish Cell GUI control 302d. The various steps of replenishing a cell 46 are numbered on the left hand side of the various replenish wizard GUIs, as illustrated (FIGS. 13A-13E). To replenish a cell 46, the following steps are performed. The stock bottle of the drug to be replenished is retrieved and the cell to be replenished is located. On the Cell Inventory GUI 200, an operator touches the Replenish Wizard GUI control 302d. The replenish wizard appears and the operator is directed to scan the NDC barcode on the stock bottle to verify that the correct drug is being added to a cell 46 via scanner 49 or 50. Alternatively, a pop-up keyboard may be used to enter the NDC number manually. The operator then enters the lot number on the stock bottle using the pop-up keypad. The operator then touches the stock bottle expiration GUI control and selects the month/year from the month/year drop-down list. The operator then touches the Add GUI control and enters the number of pills to be added to the cell 46 using the pop-up keypad. The operator then adds pills to the cell 46, closes the cell door and touches the complete GUI control.

Return-to-Stock Wizard

Figure 14A:
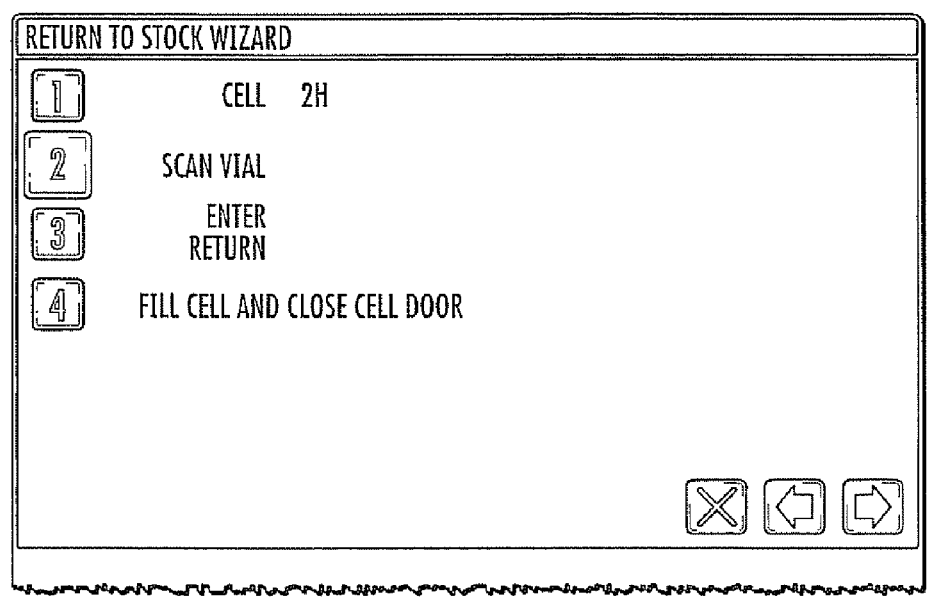
Figure 14B:
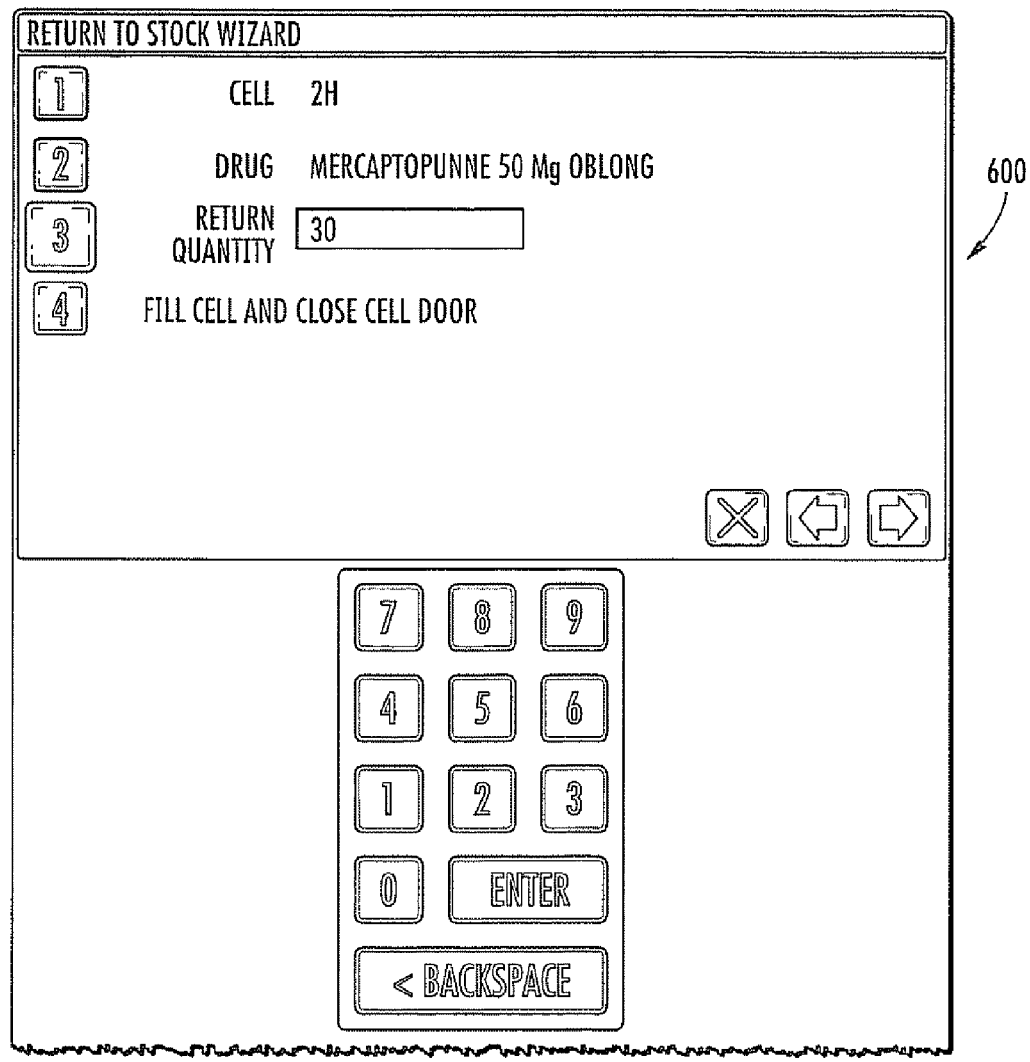
Figure 14C:
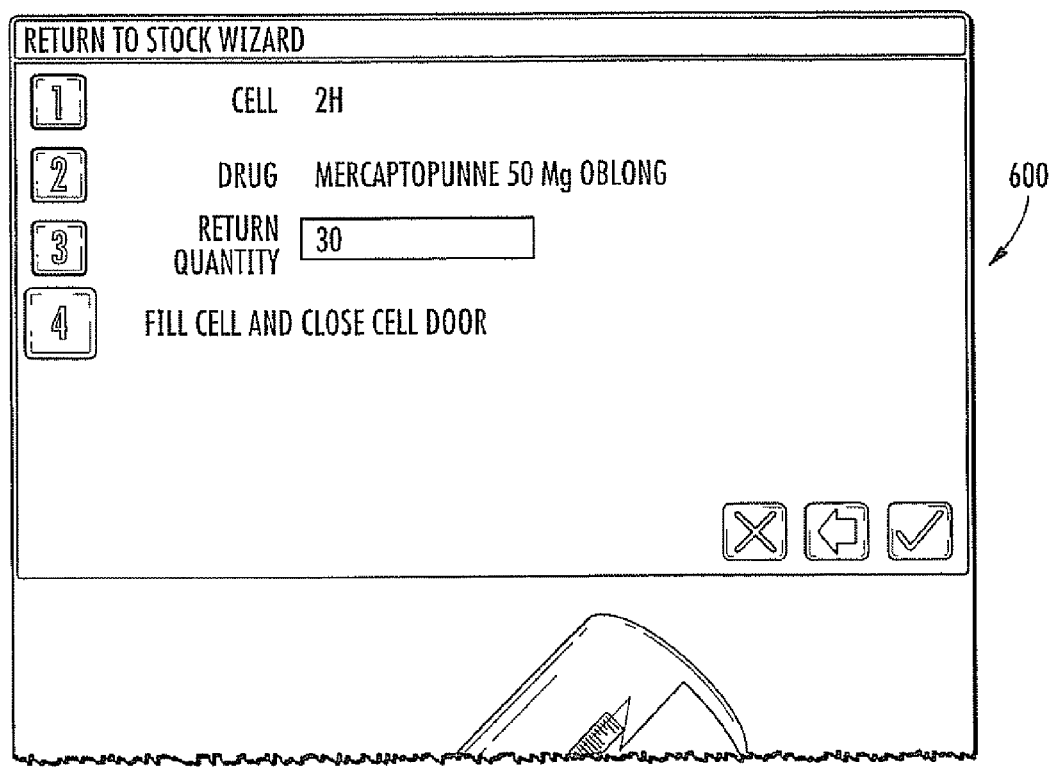
Figure 15A:
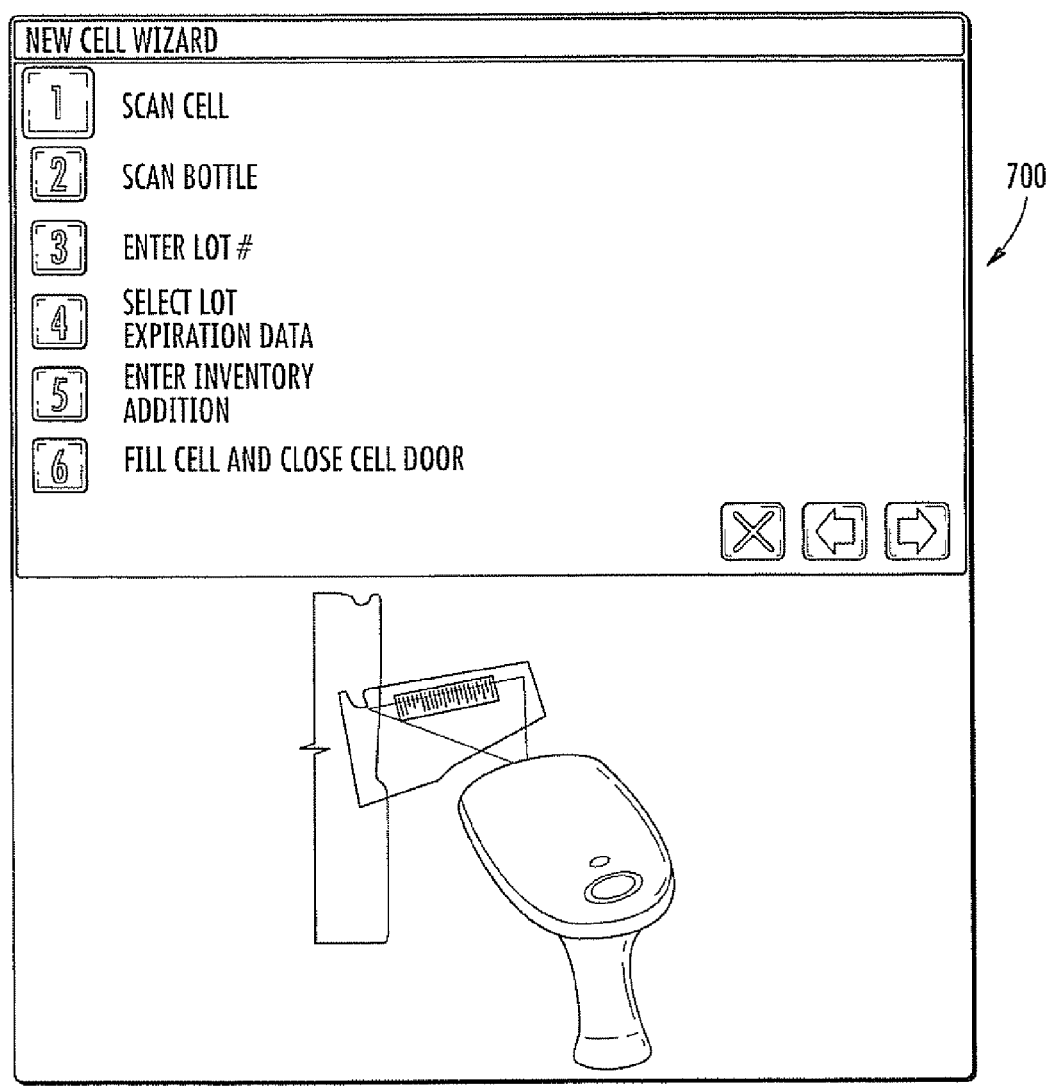
Figure 15B:
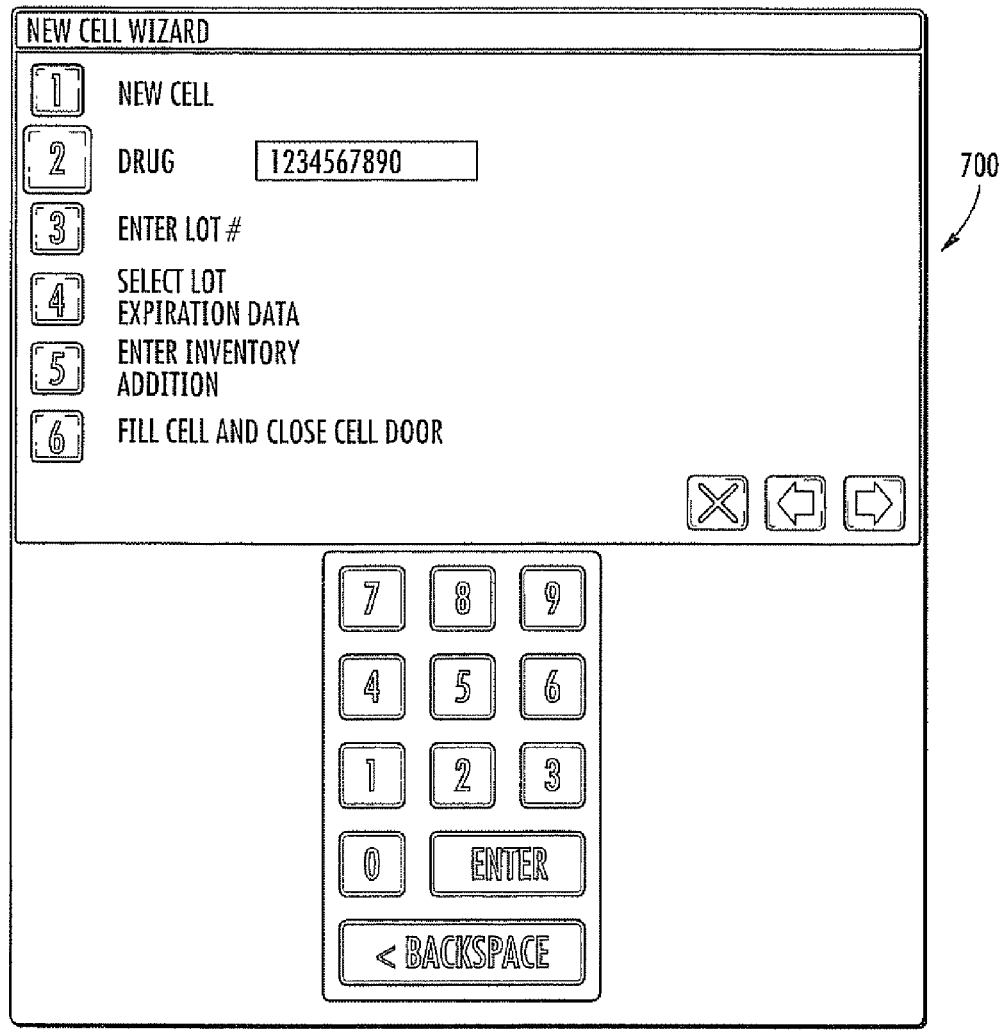
Figure 15C:
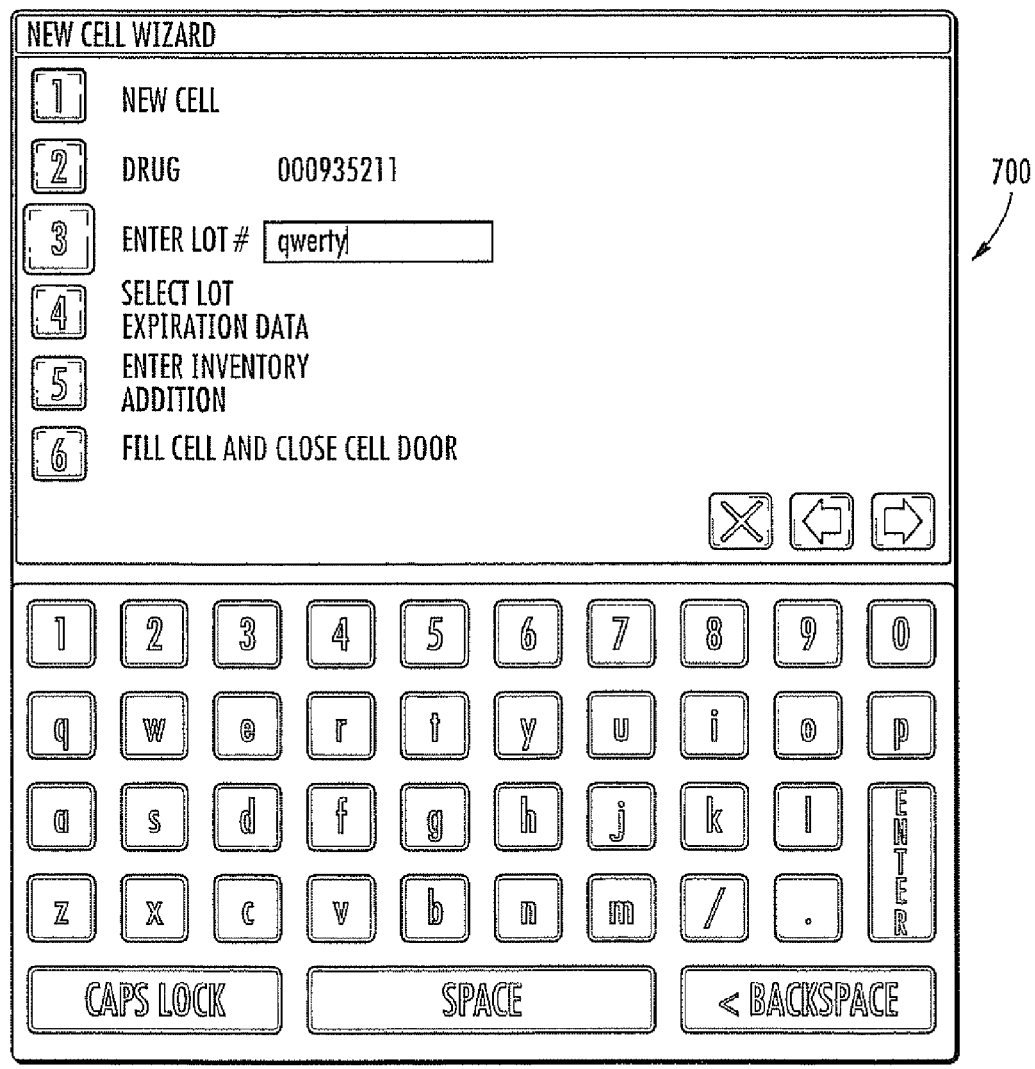
Figure 15F:
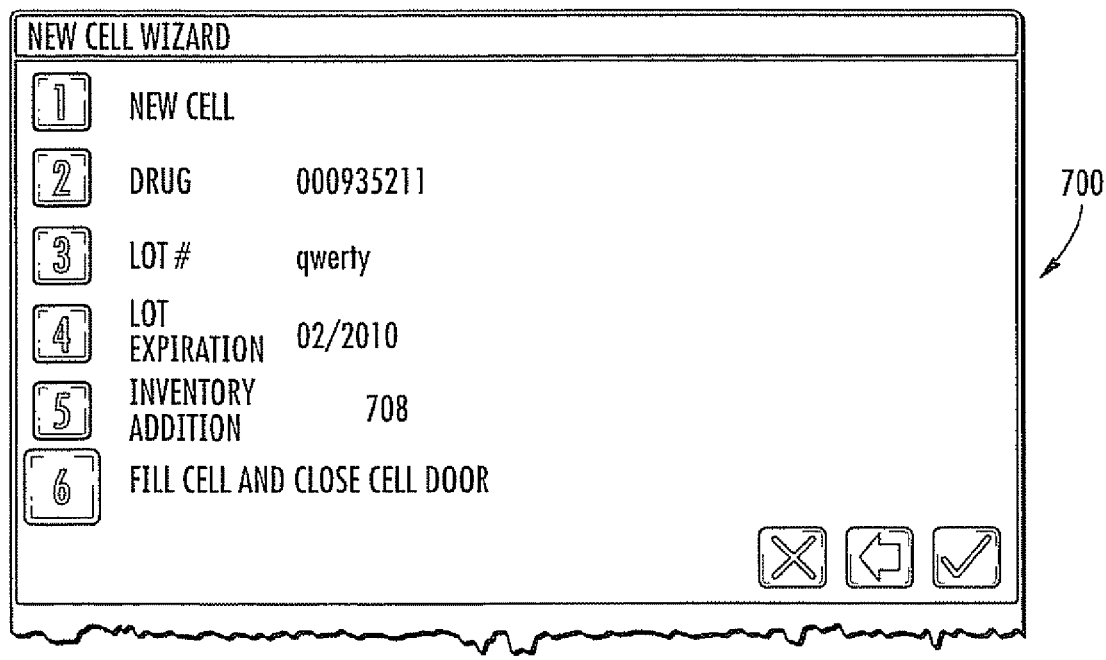

Referring now to FIGS. 14A-14C, the return-to-stock (RTS) wizard 600 will now be described. The RTS procedure is used to return partial prescription fills, calibration fills, and unclaimed prescription orders to the system 40. RTS procedures are performed on the replenishing side of the system 40. To perform an RTS procedure, a barcode on the pill container containing pills to be returned to stock is scanned, for example via scanner 49 or 50, and the RTS Wizard starts automatically. Alternatively, the user can open the RTS Wizard by touching the RTS Wizard GUI control 302c in the Parameters GUI 300. The indicator light flashes on the cell from which the prescription was filled to identify to the operator the correct cell 46 for the pills being returned. The operator then scans a barcode associated with the identified cell 46. If the scan indicates that an operator is attempting to return pills to the wrong cell 46, an error message is displayed. The pill quantity is automatically calculated and displayed. The displayed value is the quantity of pills that were dispensed for this prescription order. For example, if only 9 pills were dispensed for a prescription order requiring 10 pills, the displayed return quantity is 9. The operator then empties the contents of the container into the correct cell 46. The operator then touches the complete GUI control to conclude operations.

New Cell Wizard

Referring now to FIGS. 15A-15E, a New Cell wizard 700 is illustrated that is used for setting up and calibrating a cell 46 to house a drug already specified in the Master Drug List (MDL). The MDL is an internally maintained database of the pharmaceutical dispensing system 40 that includes all the drug dispensing information for each drug in the system's inventory. The New Cell wizard 700 is launched via the New Cell GUI control 202c in the Cell Inventory GUI 200 (FIG. 9).

To set up a new cell, an operator launches the New Cell wizard via New Cell GUI control 202c. The cell door of the new cell 46 is opened and the bar code associated with the cell 46 is scanned via scanner 50. The bar code on the stock bottle 46 is also scanned. Alternatively, the NDC of the drug can be entered manually via a pop-up keypad. The operator enters the Lot number of the drug, the Lot expiration date, and the pill quantity being added to the cell 46. The pills are then added to the cell 46 and the cell door is closed.

New Drug Wizard

Figure 16A:
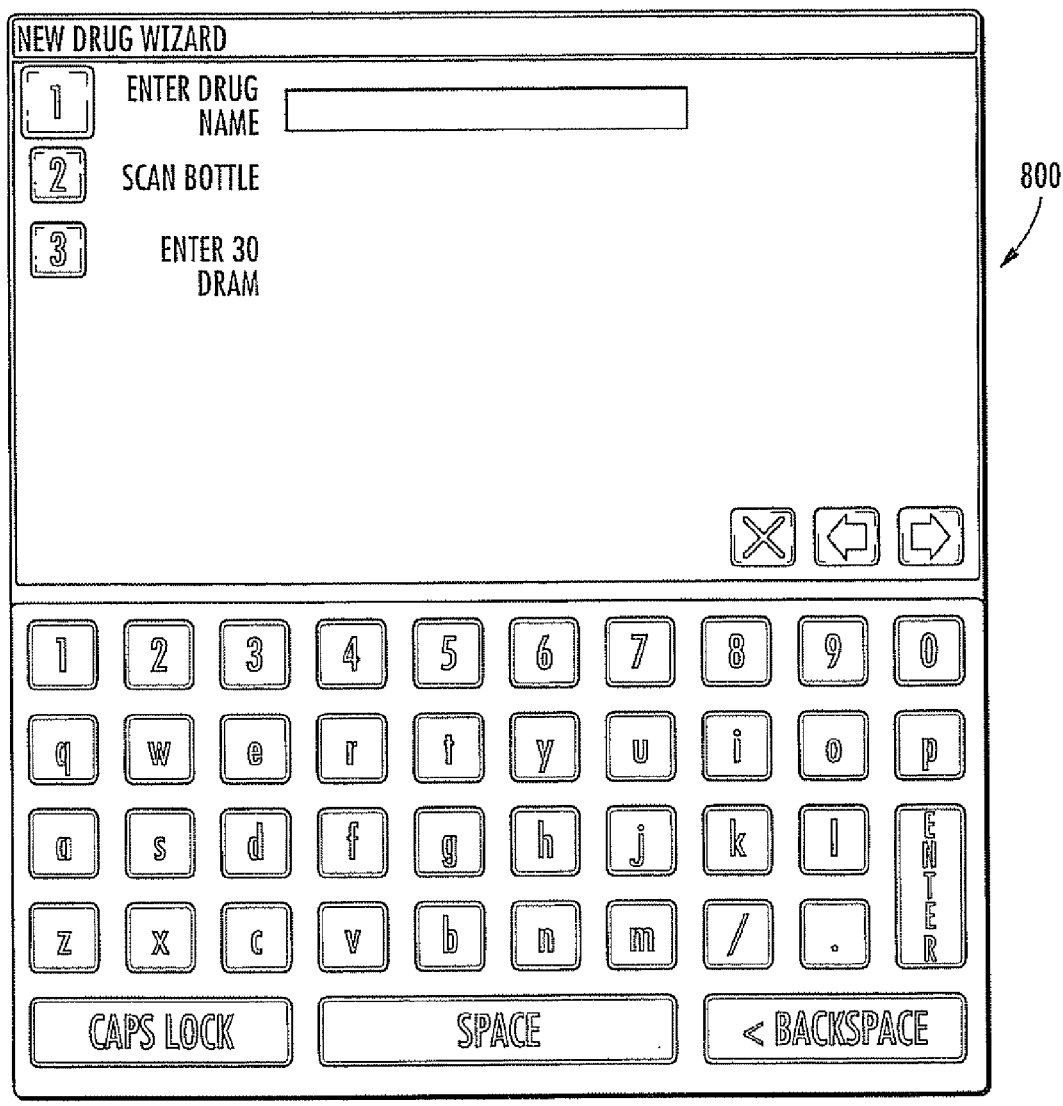
Figure 16B:
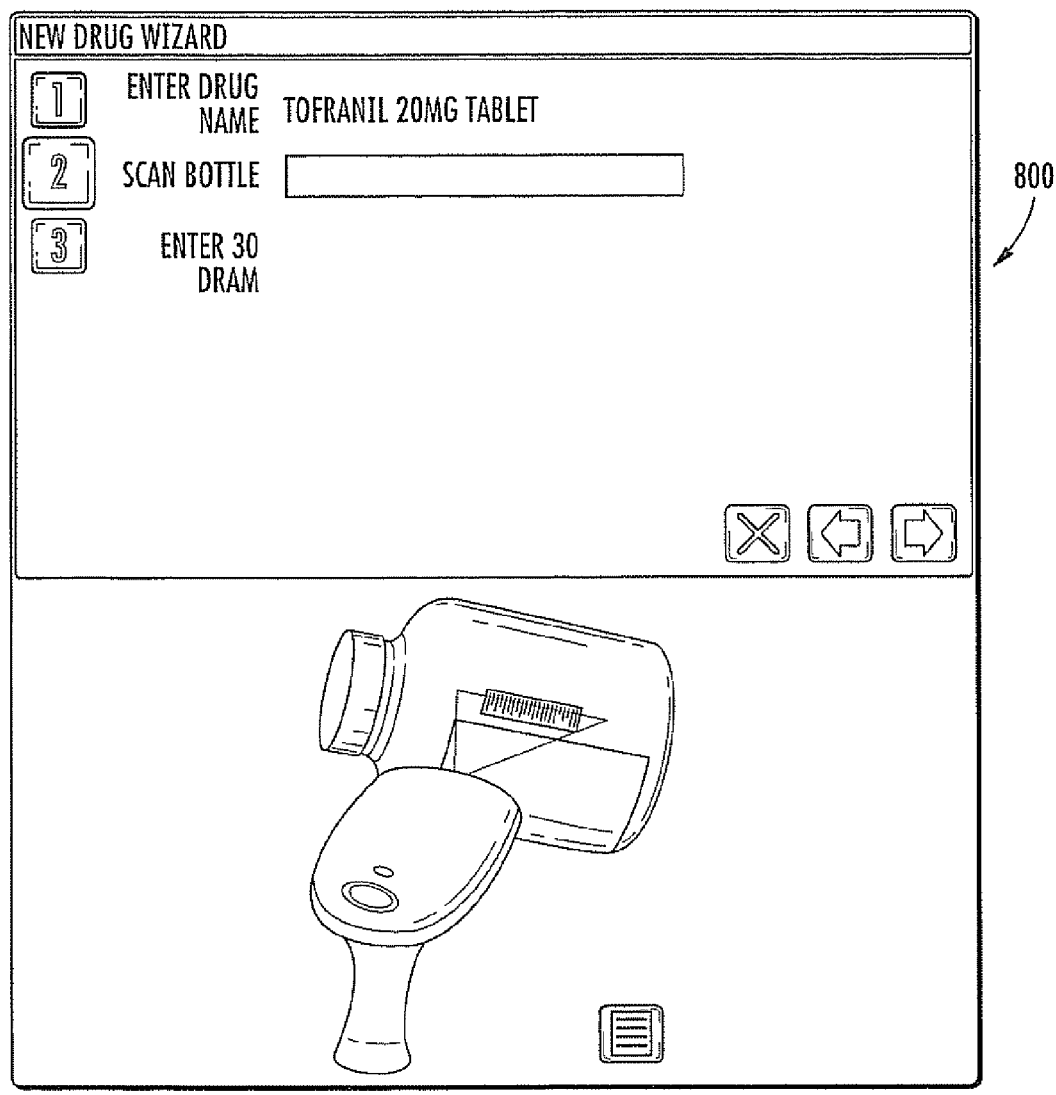
Figure 16C:
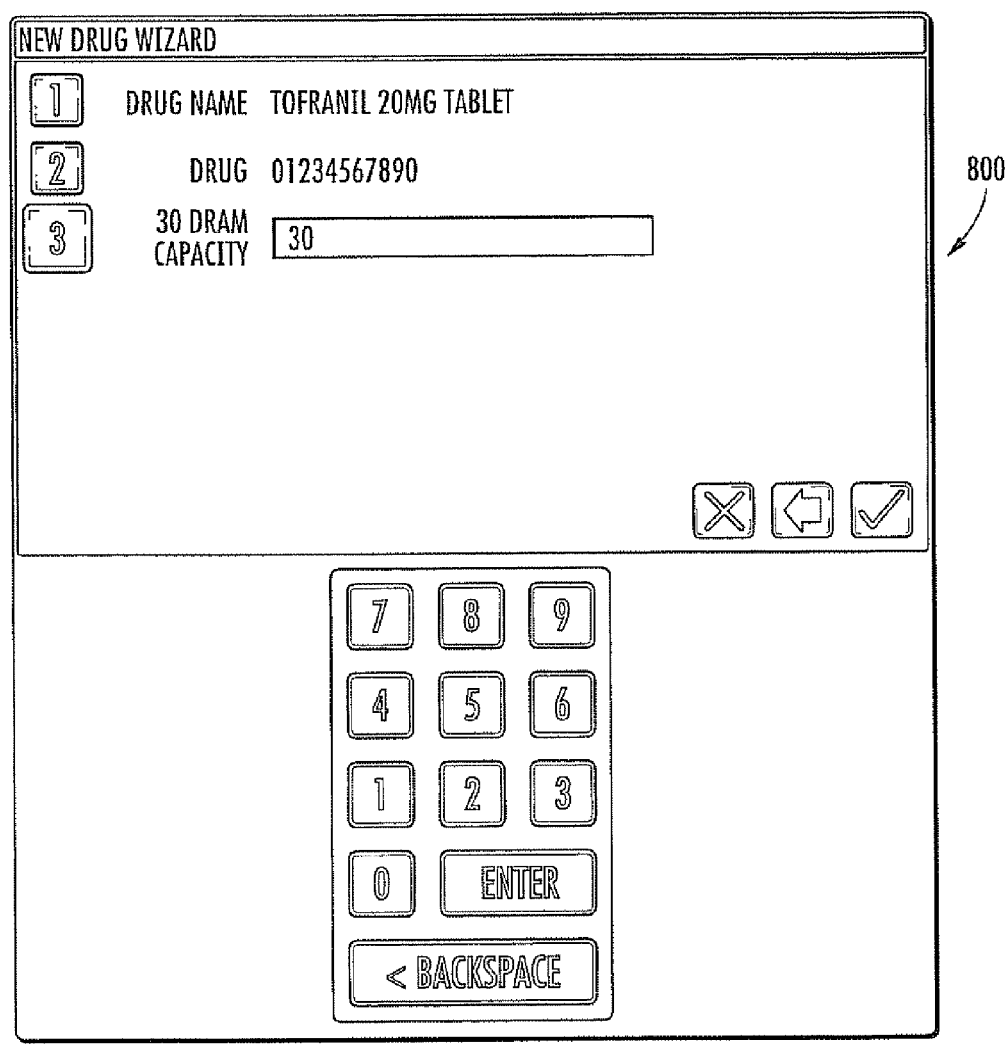

Referring now to FIGS. 16A-16C, adding a new drug to the system 40 will be described. An operator uses the New drug wizard 800 to add a new drug to the pharmaceutical dispensing system 40. A new drug is one not currently described in the MDL of the pharmaceutical dispensing system 40. Operations for adding a new drug to the pharmaceutical dispensing system 40 are performed on the replenishing side of the system 40. A new drug can be added to inventory at any time including while the pharmaceutical dispensing system 40 is in run mode and processing prescription orders.

The various steps of adding a new drug are numbered on the left hand side of the various add drug wizard GUIs, as illustrated (FIGS. 16A-16C). From the Cell Inventory GUI 200, an operator touches the New Drug Wizard GUI control 202b. The operator then enters the drug name using the pop-up keyboard. The new drug wizard then directs the operator to scan the barcode on the stock bottle via scanner 49 or 50, or to touch the NDC GUI control and enter the NDC manually using the pop-up keyboard. The operator then enters the thirty Dram capacity for the drug using the pop-up keypad (thirty dram capacity is required so that the system 40 can calculate how many pill containers are needed to fill any given prescription order based on the number of pills ordered).

Reports

The pharmaceutical dispensing system 40 includes a reports component, which allows an operator to build, run, export, and print reports. Exemplary reports are identified in Table 1 below. However, embodiments of the present invention are not limited to the identified reports.

TABLE 1

| Report | Description |
| --- | --- |
| Cleared Shelf | Lists prescription orders for a designated date range that were marked as "Shelf Cleared." |
| Dispense | Lists prescription orders filled by the automated pharmacy system during a designated date range. |
| Drug Prescription History | Lists all drugs dispensed by the automated pharmacy system during a designated date range. |
| Drug Setup | Displays all cells that were set up with a drug during a designated date range. |
| Inventory by Cell | Displays the inventory for each cell in the automated pharmacy machine |
| Inventory by Drug Code | Displays the automated pharmacy system's inventory by drug code |
| Lot Usage | Lists all prescription orders and the Lot number used to fill each prescription order for a given drug code. If a Lot number is specified, this report lists only those orders filled with the given drug code and Lot number. |
| Low Cell | Lists all cells with inventory less than the drug's low inventory threshold. |
| Order Detail | Displays all details for a specific prescription order. These include the states the order passed through in the unit, dispensing cell information and dispensing shelf location. |
| Replenish | Lists all replenishments and Return to Stock procedures. |
| Replenishments by Day | On a bar graph, displays a replenishment count grouped by hour for a specified day. |
| Prescription Volume by Day | On a bar graph, displays a count of prescription orders submitted to the automated pharmacy system and prescriptions picked up from the automated pharmacy system, grouped by hour for a specified day. |
| Prescription Volume by Drug Code | Displays a summary of the number of dispensed pills and prescriptions, grouped by drug code and a time period (day/month/year). |

Referring to FIGS. 17A-17G, operations for building, running, viewing, exporting, and printing reports (e.g., any of the reports listed in Table 1), according to some embodiments of the present invention will be described. Although the output of each report is different, the steps that an operator takes to generate a report generally are the same. These steps, broadly speaking, are build the report, view the report, set up a printer and print the report. Each of these steps are described below.

Table 2 below contains a description of column headings that are utilized in various ones of the reports that can be built, according to some embodiments of the present invention. However, embodiments of the present invention are not limited to the listed column headings. Other column headings may also be utilized in various embodiments of the present invention.

TABLE 2

| Column Heading | Description |
| --- | --- |
| Drug Code | The drug's NDC or DIN. |
| Drug Name | The name of the drug. |
| Entry date | Date prescription order was processed by the automated pharmacy system. |
| Loc. | Cell location. The cell ID (for example, 2B). |
| Lot Exp. | Expiration date of the stock bottle's Lot. |
| NDC Barcode | Bar code on the stock bottle identifying the drug's NDC value. Bar codes displayed in this column can be scanned via scanner. |
| Order No. | The prescription order number. |
| Qty. | Number of pills dispensed to fill a specific prescription order. |
| Vial No. | The number of vials needed to contain all of the pills for a prescription order. |
| Total Qty | Total number of pills dispensed per prescription order. |
| Script Total | Total number of prescriptions for a given drug. |
| Date Filled | Date prescription order was filled. |
| Script Count | Number of prescriptions filled for a given drug code. |
| Avg Pills/Script | Average number of pills per prescription for a given drug code. |
| Total Fill Qty | Total number of pills dispensed for a given drug code. |
| Replenish Date | Date a given cell was replenished. |
| Orig Qty | Original inventory in a cell when it was replenished. |
| Add Qty | Pill inventory added to a cell when it was replenished. |
| New Qty | Resulting inventory after a cell was replenished (Orig Qty + Add Qty). |
| Max Cap | The maximum established capacity for a cell that was replenished. |
| % Repl | Of the available pill capacity in a cell, the percentage that was replenished. |
| Total Qty. | Total number of pills dispensed for a particular drug. |
| Total Scripts | Total number of prescriptions processed for a particular drug. |

According to some embodiments of the present invention, an operator builds a report on the dispensing side of the pharmaceutical dispensing system 40 by activating the System Functions GUI control 170b in the Home GUI 100 and then activating a "launch" GUI control that is displayed. In response, a reports GUI 900 is displayed as illustrated in FIG. 17A. An operator may also build reports on the replenishing side of the automated pharmacy system 40 by activating a System Functions GUI (or similar GUI control) in any of the replenishing side GUIs described above.

In the illustrated embodiment, the reports GUI 900 shown in FIG. 17A includes three separate GUIs: Build Report 910, View Report 920, and Setup 930. Each of these GUIs is displayed when an operator touches a respective tab 910a, 920a, 930a, as illustrated. The Build Report GUI 910 has three separate elements: Select Report 912, Report Parameters 914, and Apply Sorting 916. The Select Report element 912 displays a list of reports that an operator can select. To build a report, an operator selects a report from this list, as illustrated in FIG. 17B. In FIG. 17B, the operator has selected the "Dispense Info" report.

Figures 17C, 17D, 17E:
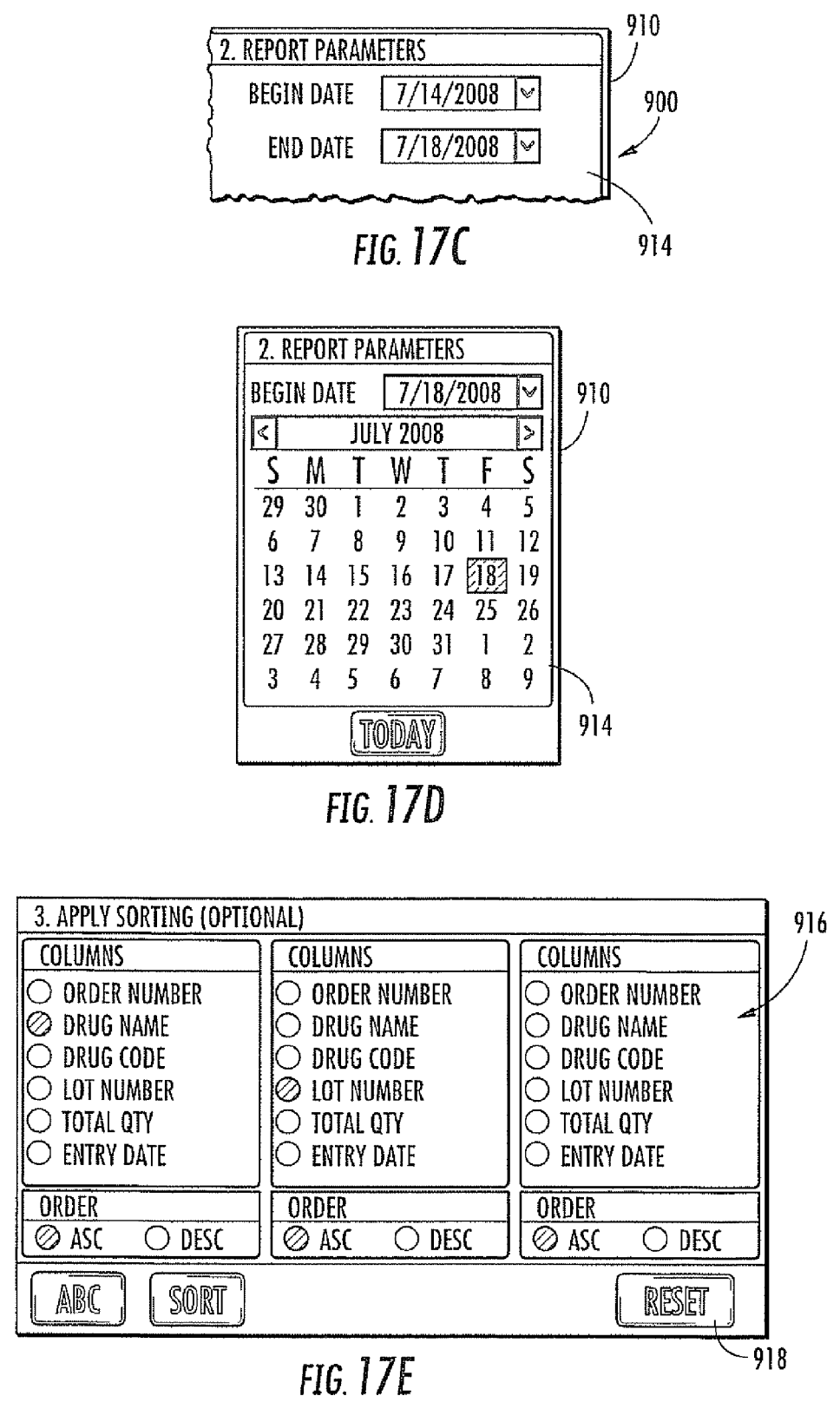

After selecting a report, the report parameters, such as begin date and end date, are defined in the Report Parameters element 914, as illustrated in FIG. 17C. Not all reports have selectable parameters, however. In the illustrated report, an operator is selecting a date range for the "Dispense Info" report. The "Dispense Info" report will display all of the prescription orders filled by the pharmaceutical dispensing system 40 during the specified time period. As illustrated in FIG. 17D, a pop-up calendar can be displayed for use in selecting begin dates and end dates.

Referring to FIG. 17E, the Apply Sorting element 916 may be utilized to sort the output of various columns of a selected report (e.g., ascending order, descending order, etc.). In the illustrated Apply Sorting element 916 displayed in FIG. 17E, the operator has decided to sort by drug name in ascending order, and to sort by drug lot number in ascending order. The Reporting GUI displayed in FIG. 17E also includes a Reset GUI control 918 that allows an operator to start over and reenter desired sorting and report parameter criteria. When sorting with multiple columns, as illustrated in FIG. 17E, sorting is performed from left to right, according to some embodiments of the present invention. For example, if an operator selects "Entry Date" in the first column of FIG. 17E, and selects "Drug Code" in the second column of FIG. 17E, a report will be sorted such that drug codes for each entry date will be displayed. Further, if an operator selects "Lot Number" in the third column of FIG. 17E, the above-described report will be sorted such that lot numbers for each drug code will be displayed. In other words, for each entry date, a list of drug codes will be displayed, and for each drug code, a list of lot numbers will be displayed. Embodiments of the present invention, however, are not limited to this type of sorting. Various ways of sorting information for reports may be utilized without limitation.

Figure 17F:
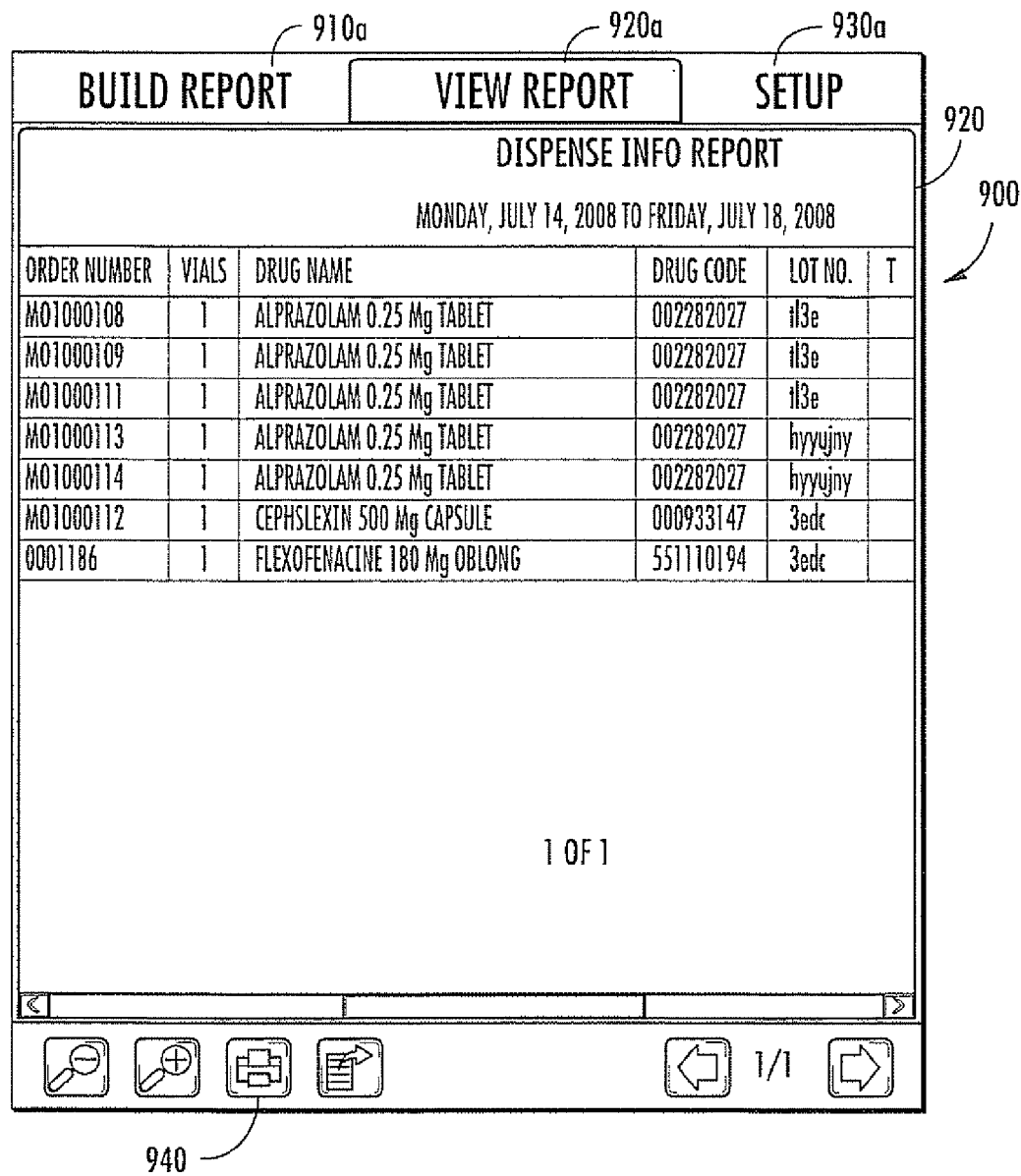

Once a report is built it can be viewed by touching the View Report tab 920a, which displays the View Report GUI 920, as illustrated in FIG. 17F. The operator can manipulate vertical and horizontal scroll bars that are provided when a report is displayed to view hidden regions of the report, as would be understood by those skilled in the art. In addition, zoom-in and zoom-out tools are provided to enlarge and reduce the displayed size of a report.

Figure 17G:
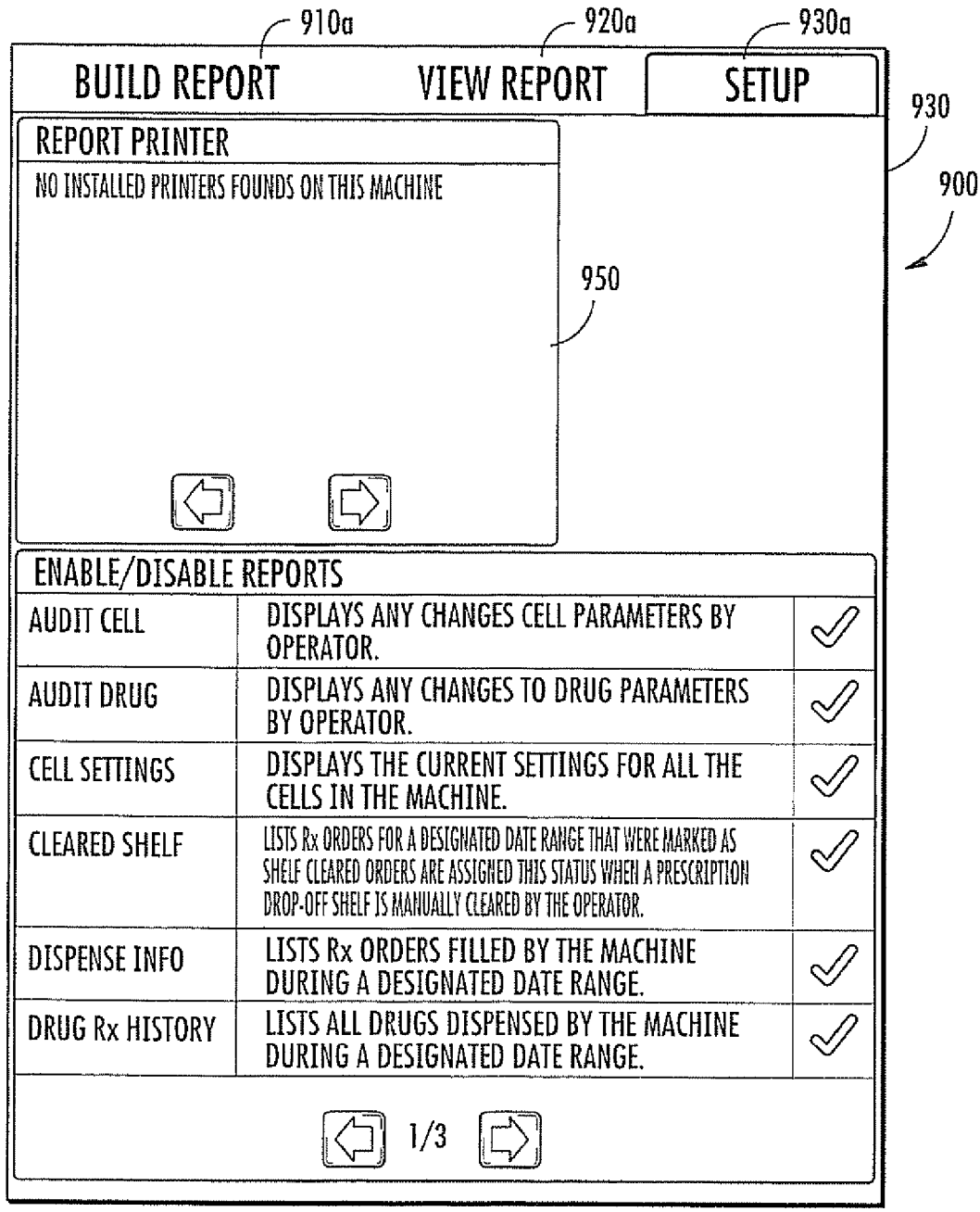

At this point, an operator can choose to print the viewed report or to run the report again with different parameters. To run the report with different parameters, the operator touches the Build Report tab 910a, which displays the Build Report GUI 910, selects new parameters, and touches the View Report tab 920a, which displays the View Report GUI 920, to rerun the report. To print the viewed report, the operator touches the print GUI control 940. However, prior to printing, the operator needs to designate a printer using the Setup GUI 930. To designate a printer, the operator touches the Setup tab 930a, which displays the Setup GUI 930, and then selects a printer from the Select Printer GUI 950, as illustrated in FIG. 17G.

Reports can also be exported to other applications and printed from those applications. For example, a report can be exported to a spreadsheet application. When an operator chooses to export a report, the report format is rendered in comma-separated format and is saved to a pre-designated location on the pharmaceutical dispensing system 40. The pharmaceutical dispensing system 40 uniquely names each exported file. In some embodiments, an exported file is saved in ".csv format" in the form <ReportName_Date_Time-Stamp>. However, embodiments of the present invention are not limited to a particular file format for exporting. Other file formats may be utilized.

Device Relationship Management (DRM)

The pharmaceutical dispensing system 40 includes a Device Relationship Management (DRM) component, which provides the following: health monitoring functions for the pharmaceutical dispensing system 40; local DRM data storage, and a guaranteed data delivery mechanism. Information about the health of the pharmaceutical dispensing system 40 is gathered by a variety of health monitoring functions, which report sensor values (particularly during critical portions of operation of the system 40), error occurrences, results of periodically performed built-in-tests, and high level machine events.

Sensors may be configured to monitor temperature and/or pressure of various components of the pharmaceutical dispensing system 40. In addition, the number and/or percent of prescription order filling failures can be monitored. Errors caused by robotic arm 68 move errors, capper, labeler or other subsystem errors can be monitored. High level machine events can include counting problems, power outages, etc. Built-in tests that can be performed include a system health test that automatically runs on start up to check all of the components of the pharmaceutical dispensing system 40.

This information is held as time-stamped data in a Local DRM Data Storage facility, specifically a SQL Server Database. The guaranteed data delivery mechanism is implemented as part of a software service that pulls information from the database and either a) transmits it over a secure network connection; or b) downloads it to a removable medium, such as a flash drive.

Figure 18:
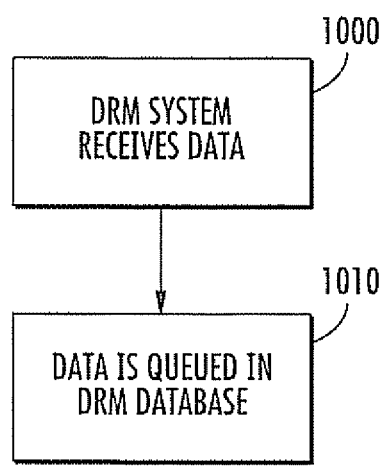
FIGS. 18-19 are flow charts illustrating operations of a Device Relationship Management (DRM) component for the pharmaceutical dispensing system of FIGS. 2-3, in accordance with some embodiments of the present invention.
Figure 19:
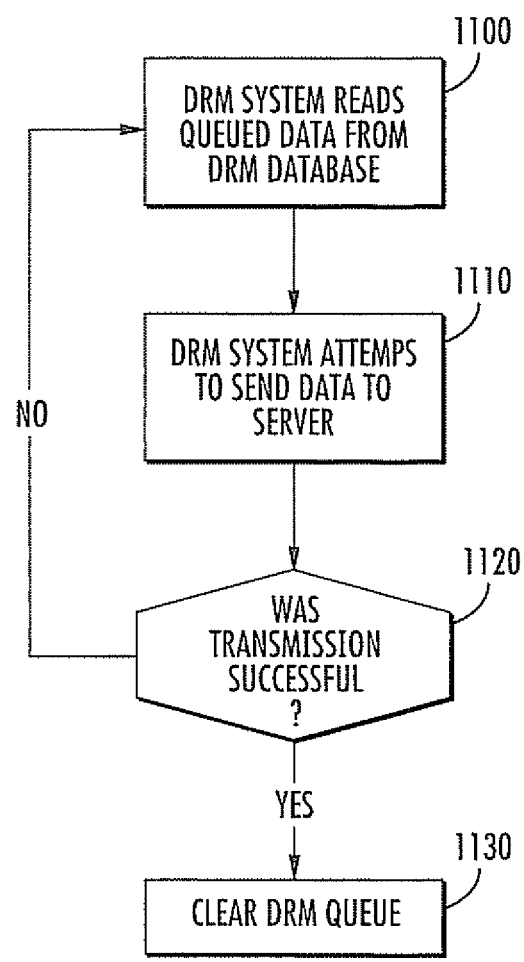

Referring to FIGS. 18-19, the DRM system also includes a reliable message delivery system. This system guarantees that in the event of a network outage, power outage, or other situation which causes the system to be unable to send data, no data will be lost until the outage is resolved. When data is received (Block 1000), it is queued in a database (Block 1010). The system reads queued data from the DRM database (Block 1100) and attempts to send the data back to the DRM server (Block 1110). If the transmission was successful and receipt is acknowledged (Block 1120), the data is removed from the queue (Block 1130); otherwise, the data remains in the queue and transmission is retried at the next opportunity.

Figure 20:
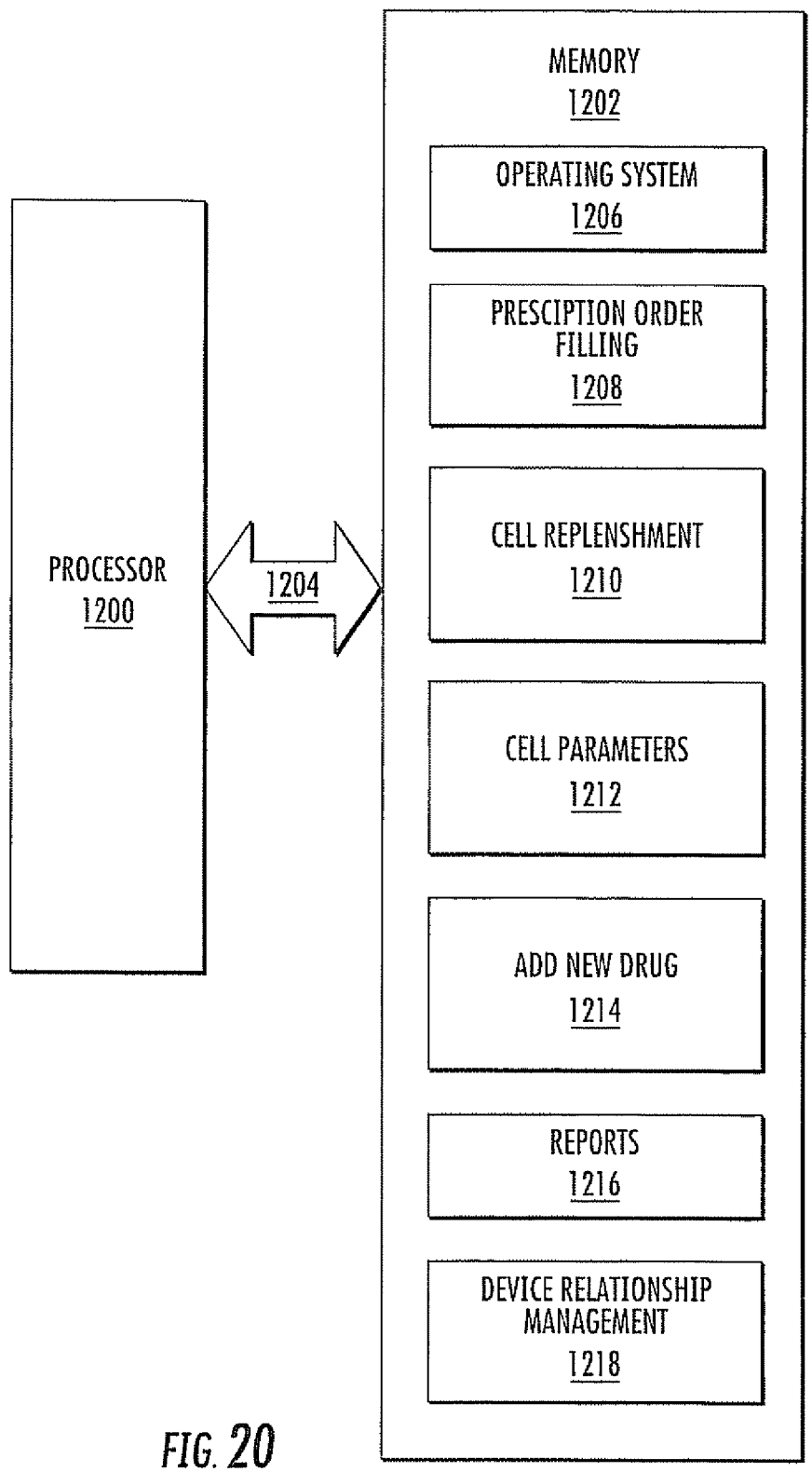
FIG. 20 is a block diagram that illustrates a software architecture for implementing operations of the pharmaceutical dispensing system of FIGS. 2-3, in accordance with some embodiments of the present invention.

FIG. 20 illustrates a processor 1200 and a memory 1202 that may be used to implement the operations of the pharmaceutical dispensing system 40 of FIGS. 2-3, according to some embodiments of the present invention. For example, in some embodiments of the present invention, the processor 1200 and memory 1202 may be used to embody the processors and the memories used in automatically filling prescription orders, in replenishing pills within cells 46, in modifying parameters of cells 46, in adding new drugs to inventory, in creating reports, etc.

The processor 1200 communicates with the memory 1202 via an address/data bus 1204. The processor 1200 may be, for example, a commercially available or custom microprocessor. The memory 1202 is representative of the overall hierarchy of memory devices containing the software and data used to automatically fill prescription orders, to replenish pills within cells 46, to modify parameters of cells 46, and to add new drugs to inventory, to generate reports, and to perform device relationship management, in accordance with some embodiments of the present invention. The memory 1202 may include, but is not limited to, the following types of devices: cache, ROM, PROM, EPROM, EEPROM, flash, SRAM, and DRAM.

As shown in FIG. 20, the memory 1202 may hold seven or more major categories of software and data: an operating system 1206, a prescription order filling module 1208, a cell replenishment module 1210, a cell parameters module 1212, a new drug module 1214, a reports module 1216, and a Device Relationship Management (DRM) module 1218. The operating system 1206 controls operations of the prescription order filling module 1208, cell replenishment module 1210, cell parameters module 1212, new drug module 1214, reports module 1216, and DRM module 1218.

The prescription order filling module 1208 comprises logic for processing prescription orders as described above with respect to the various dispensing side GUIs. The cell replenishment module 1210 comprises logic for monitoring/controlling/modifying drug inventory in each of the cells 46, as described above with respect to the various replenishing side GUIs. The cell parameters module 1212 comprises logic for monitoring/controlling/modifying parameters for each of the cells 46, as described above with respect to the various replenishing side GU Is. The new drug module 214 comprises logic for adding a new drug to a cell 46, as described above with respect to the various replenishing side GUIs. The reports module 1216 comprises logic for building, running, exporting, and printing reports from either side of the pharmaceutical dispensing system 40, as described above with respect to FIGS. 17A-17G. The DRM module 1218 comprises logic for handling and transmitting data to and from the pharmaceutical dispensing system 40, as described below with respect to FIGS. 18-19.

Although FIG. 20 illustrates an exemplary software architecture that may facilitate automatically filling prescription orders, replenishing pills within cells 46, modifying parameters of cells 46, adding a new drug to inventory, generating reports, and performing device relationship management functions, it will be understood that the present invention is not limited to such a configuration, but is intended to encompass any configuration capable of carrying out the operations described herein.

Computer program code for carrying out operations of the prescription order filling module 1208, cell replenishment module 1210, cell parameters module 1212, new drug module 1214, reports module 1216, and DRM module 1218 may be written in a high-level programming language, such as Python, Java, C, and/or C++, for development convenience. In addition, computer program code for carrying out operations of embodiments of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A pharmaceutical dispensing system, comprising:
   a frame having first and second opposed sides;
   a plurality of cells attached to the frame and configured to house pharmaceutical pills, each of the cells being accessible from the first side of the frame for replenishment of pharmaceutical pills therein;
   a plurality of dispensing shelves attached to the frame and configured to receive filled pill containers, each of the shelves being accessible from the second side of the frame for removal of filled pill containers therein, wherein the dispensing system labels empty pill containers, fills each labeled pill container with pills from a respective one of the cells, and then deposits each filled pill container in a respective one of the dispensing shelves of the pharmaceutical dispensing system;
   a first touch screen display on the frame first side;
   a second touch screen display on the frame second side;
   a processor;
   memory coupled to the processor;
   a computer program residing in the memory that is executable by the processor for displaying a cell inventory graphical user interface (GUI) within the first touch screen display, wherein the cell inventory GUI displays cell inventory information, and wherein the cell inventory GUI comprises one or more GUI controls that are responsive to user touching for adding and/or modifying contents of the cells; and
   a computer program residing in the memory that is executable by the processor for displaying a series of GUIs within the second touch screen display, wherein each GUI in the series comprises status information about a prescription order at a respective stage of completion of the prescription order by the pharmaceutical dispensing system, wherein the series of GUIs comprises a ready queue GUI that displays an array of icons, each icon associated with a respective dispensing shelf of the pharmaceutical dispensing system, and wherein each icon displays a number of filled pill containers in a respective dispensing shelf of the pharmaceutical dispensing system.

2. The system of claim 1, wherein the cell inventory GUI displays a graphical representation of each cell.

3. The system of claim 1, wherein the series of GUIs comprises a pending queue GUI that displays information about pending prescription orders.

4. The system of claim 1, wherein the series of GUIs comprises a complete queue GUI that displays information about filled prescription orders that have been removed from dispensing shelves of the pharmaceutical dispensing system.

5. The system of claim 1, wherein the ready queue GUI comprises a GUI control that is responsive to user touching, and wherein a graphical representation of a dispensing shelf where a filled pill container is located is displayed in response to user touching of the GUI control.

6. The system of claim 1, wherein the series of GUIs comprises a ready shelf GUI that is a graphical representation of the dispensing shelves of the pharmaceutical dispensing system.

7. The system of claim 1, wherein the series of GUIs comprises an incomplete queue GUI that displays information about unfilled prescription orders.

8. The system of claim 2, wherein the graphical representation of each cell is displayed in a color that indicates an inventory level of pharmaceutical pills therein.

9. The system of claim 1, further comprising a computer program residing in the memory that is executable by the processor for displaying a report builder GUI within the first and second touch screen displays, wherein the report builder GUI is configured to build reports relating to one or more of the following: pending prescription orders, filled prescription orders, cell inventory information, and drug information.

10. The system of claim 1, further comprising a computer program residing in the memory that is executable by the processor for monitoring selected functions of the pharmaceutical dispensing system and for storing selected parameters associated with the monitored functions.

11. A pharmaceutical dispensing system, comprising:
    a frame having first and second opposed sides;
    a plurality of cells attached to the frame and configured to house pharmaceutical pills, each of the cells being accessible from the first side of the frame for replenishment of pharmaceutical pills therein;
    a plurality of dispensing shelves attached to the frame and configured to receive filled pill containers, each of the shelves being accessible from the second side of the frame for removal of filled pill containers therein, wherein the dispensing system labels empty pill containers, fills each labeled pill container with pills from a respective one of the cells, and then deposits each filled pill container in a respective one of the dispensing shelves of the pharmaceutical dispensing system;
    a first touch screen display on the frame first side;
    a second touch screen display on the frame second side;
    a processor;
    memory coupled to the processor;
    a computer program residing in the memory that is executable by the processor for displaying a cell inventory graphical user interface (GUI) within the first touch screen display, wherein the cell inventory GUI displays cell inventory information, and wherein the cell inventory GUI comprises one or more GUI controls that are responsive to user touching for adding and/or modifying contents of the cells; and
    a computer program residing in the memory that is executable by the processor for displaying a series of GUIs within the second touch screen display, wherein each GUI in the series comprises status information about a prescription order at a respective stage of completion of the prescription order by the pharmaceutical dispensing system, wherein the series of GUIs comprises a ready queue GUI that displays an array of icons, each icon associated with a respective dispensing shelf of the pharmaceutical dispensing system, wherein each icon displays a number of filled pill containers in a respective dispensing shelf of the pharmaceutical dispensing system, and wherein a graphical representation of a respective dispensing shelf of the pharmaceutical dispensing system is displayed in response to user touching of a respective icon.

12. The system of claim 11, wherein the cell inventory GUI displays a graphical representation of each cell.

13. The system of claim 11, wherein the series of GUIs comprises a pending queue GUI that displays information about pending prescription orders.

14. The system of claim 11, wherein the series of GUIs comprises a complete queue GUI that displays information about filled prescription orders that have been removed from the dispensing shelves.

15. The system of claim 11, wherein the series of GUIs comprises a ready shelf GUI that is a graphical representation of the dispensing shelves.

16. The system of claim 11, wherein the series of GUIs comprises an incomplete queue GUI that displays information about unfilled prescription orders.

17. The system of claim 12, wherein the graphical representation of each cell is displayed in a color that indicates an inventory level of pharmaceutical pills therein.

18. The system of claim 11, further comprising a computer program residing in the memory that is executable by the processor for displaying a report builder GUI within the first and second touch screen displays, wherein the report builder GUI is configured to build reports relating to one or more of the following: pending prescription orders, filled prescription orders, cell inventory information, and drug information.

19. The system of claim 11, further comprising a computer program residing in the memory that is executable by the processor for monitoring selected functions of the pharmaceutical dispensing system and for storing selected parameters associated with the monitored functions.

* * * * *